US008492418B2

(12) United States Patent
Woods

(10) Patent No.: US 8,492,418 B2
(45) Date of Patent: Jul. 23, 2013

(54) METHOD OF TREATING SCHIZOPHRENIA PRODROME

(75) Inventor: Scott W. Woods, East Haven, CT (US)

(73) Assignee: Yale University, New Haven, CT (US)

( * ) Notice: Subject to any disclaimer, the term of this patent is extended or adjusted under 35 U.S.C. 154(b) by 30 days.

(21) Appl. No.: 11/918,287

(22) PCT Filed: Apr. 11, 2006

(86) PCT No.: PCT/US2006/013444
§ 371 (c)(1),
(2), (4) Date: Oct. 11, 2007

(87) PCT Pub. No.: WO2006/110724
PCT Pub. Date: Oct. 19, 2006

(65) Prior Publication Data
US 2009/0215842 A1    Aug. 27, 2009

Related U.S. Application Data

(60) Provisional application No. 60/670,600, filed on Apr. 11, 2005.

(51) Int. Cl.
*A61K 31/195* (2006.01)
*A61K 31/221* (2006.01)
*A61K 31/42* (2006.01)
*A61P 25/18* (2006.01)

(52) U.S. Cl.
USPC ........................... 514/380; 514/551; 514/561

(58) Field of Classification Search
USPC .......................................... 514/380, 551, 561
See application file for complete search history.

(56) References Cited

U.S. PATENT DOCUMENTS

2002/0013364 A1    1/2002    Javitt

FOREIGN PATENT DOCUMENTS

| WO | WO 2005/023261 | 3/2005 |
|----|----|----|
| WO | WO 2005/040166 | 5/2005 |
| WO | WO 2005/058317 | 6/2005 |
| WO | WO 2005/058882 | 6/2005 |
| WO | WO 2005/058885 | 6/2005 |
| WO | WO 2005/087708 | 9/2005 |

OTHER PUBLICATIONS

Wolff (Medicinal Chemistry) summarizes the state of the prodrugs art. Wolff, Manfred E. "Burger's Medicinal Chemistry, 5ed, Part I", John Wiley & Sons, 1995, pp. 975-977.*
Yung (The profromal Phase of First-Episode Psychosis: Past and Current conceptualizations, Schizophrenia Bulletin, Vol, 22 No. 2, 1996, pp. 353-370).*
Abi-Saab WM, D'Souza DC, Moghaddam B, Krystal JH (1998) The NMDA antagonist model for schizophrenia—promise and pitfalls. Pharmacopsychiatry 31:104-109.
Adler CM, Goldberg TE, Malhotra AK, Pickar D, Breier A (1998) Effects of ketamine on thought disorder, working memory, and semantic memory in healthy volunteers. Biological Psychiatry 43:811-816.
Barnes TRE, Hutton SB, Chapman MJ, Mutsatsa S, Puri BK, Joyce EM (2000) West London first episode study of schizphrenia: Clinical correlates of duration of untreated psychosis. British Journal of Psychiatry 177:207-211.
Bleuler E (1911) Dementia Praecox or the Group of the Schizophrenias. New York: International Universities Press.
Breier A, Adler CM, Weisenfeld N, Su TP, Elman I, Picken L, Malhotra AK, Pickar D (1998) Effects of NMDA antagonism on striatal dopamine release in healthy subjects: application of a novel PET approach. Synapse 29:142-147.
Carpenter WT, Buchanan RW, Javitt DC, Marder SR, Schooler NR, Heresco-Levy U, Gold JM (2004) is glutamatergic therapy really efficacious in schizophrenia? (abstract). Neuropsychopharmacology 29:S 110.
Chatterton 1E, Awobuluyi M, Premkumar LS, Takahashi H, Talantova M, Shin Y, Cui J, Tu S, Sevarino KA, Nakanishi N, Tong G, Lipton SA, Zhang D (2002) Excitatory glycine receptors containing the NR3 family of NMDA receptor subunits. Nature. 415:793-798.
Chen EYH, Dunn ELW, Chen RLY, Chung KF, Tang WN, Chan WF, Miao YK, Yeung WS, Wong CK (1999) Duration of untreated psychosis and symptomatic outcome among first episode schizophrenic patients in Hong Kong. Schizphrenia Research 36:15.
Contreras PC (1990) D-serine antagonized phencyclidine- and MK-801-induced stereotyped behavior and ataxia. Neuropharmacology 29:291-293.
Comblatt BA, Lencz T, Smith CW, Correll CU, Auther AM, Nakayama E (2003) the schizophrenia prodrome revisited: a neurodevelopmental perspective. Schizophrenia Bulletin 29:633-651.
Coyle JT, Tsai G (2004) NMDA receptor function, neuroplasticity, and the pathophysiology of schizophrenia. International Review of Neurobiology 59:491-515.
Craig TJ, Bromet EI, Fennig S, Tanenberg-Karant M, Lavelle J, Galambos N (2000) Is there an association between duration of untreated psychosis and 24-month clinical outcome in a first-admission series? American Journal Psychiatry 157:60-66.
D'Souza DC, Gil R, Cassello K, Morrissey K, Abi-Saab D, White J, Sturwold R, Bennett A, Karper LP, Zuzarte E, Chamey DS, Krystal HI (2000) IV glycine and oral D-cycloserine effects on plasma and CSF amino acids in healthy humans. Biological Psychiatry. 47:450-462.
Deutch AY, Tam SY, Freeman AS, Bowers MB, Jr., Roth RH (1987) Mesolimbic and mesocortical dopamine activation induced by phencyclidine: contrasting pattern to striatal response. European Journal of Pharmacology 134:257-264.
Domino EF, Luby ED (1981) Abnormal mental states induced by phencyclidine as a model for schizophrenia. in Domino EF (ed), PCP (Phencyclidine): Historical and Current Perspectives. Ann Arbor, MI: NPP Books, pp. 401-418.

(Continued)

*Primary Examiner* — San-Ming Hui
*Assistant Examiner* — Kathrien Cruz
(74) *Attorney, Agent, or Firm* — Henry D. Coleman; R. Neil Sudol

(57) ABSTRACT

The present invention relates to a method of treating schizophrenia prodrome in human subjects using a NMDA glycine site agonist, a glycine transporter-1 inhibitor or mixtures thereof, optionally in combination with a pharmaceutically acceptable additive, carrier or excipient.

4 Claims, 8 Drawing Sheets

OTHER PUBLICATIONS

Evins AE, Alnico E, Posever TA, Toker R, Goff DC (2002) D-Cycloserine added to risperidone in patients with primary negative symptoms-of schizophrenia. Schizophrenia Research. 56:19-23.

Evins AE, Fitzgerald SM, Wine L, Rosselli R, Goff DC (2000) Placebo-controlled trial of glycine added to clozapine in schizophrenia. American Journal of Psychiatry 157:826-828.

Foucaud B, Laube B, Schemm R, Kreimeyer a, Goeldner M, Betz H (2003) Structural model of the N-methyl-D-aspartate receptor glycine site probed by site-directed chemical coupling. Journal of Biological Chemistry 278:24011-24017.

Goebel DJ, Poosch MS (1999) NMDA receptor subunit gene expression in the rat brain: a quantitative analysis of endogenous rnRNA levels of NRICom, NR2A, NR2B, NR2C, NR2D and NR3A. Brain Research. Molecular Brain Research 69:164-170.

Goff DC, Tsai G, Levitt J, Amico E, Manoach D, Schoenfeld DA, Hayden DL, McCarley R, Coyle JT (1999) A placebo-controlled trial of D-cycloserine added to conventional neuroleptics in patients with schizophrenia.[see comment]. Archives of General Psychiatry 56:21-27.

Goff DC, Tsai G, Manoach DS, Coyle JT (1995) Dose-finding trial of D-cycloserine added to neuroleptics for negative symptoms in schizophrenia. American Journal of Psychiatry 152:1213-1215.

Goff DC, Tsai G, Manoach DS, Flood J, Darby DG, Coyle JT (1996) D-cycloserine added to clozapine for patients with schizophrenia. American Journal of Psychiatry 153:1628-1630.

Hafaer H, Maurer K, Loffler W, Riecher-Rossler A (1993) The influence of age and sex on the onset and early course of schizophrenia. Br J Psychiatry 162:80-86.

Hashimoto A, Nishikawa T, Hayashi T, Fujii N, Harada K, Oka T, Takahashi K (1992) the presence of free D-serine in rat brain. FEBS Letters 296:33-36.

Hawkins KA, Addington J, Keefe RSE, Christensen B, Perkins DO, Zipurksy R, Woods SW, Miller TJ, Marquez E, Breier A, McGlashan TH (2004a) Neuropsychological status of subjects at high risk for a first episode of psychosis. Schizophrenia Research 67:115-122.

Hawkins KA, Qninlan D, Miller TJ, McGlashan TH, Zipursky RB, Perkins DO, Addington J, Woods SW (2004b) Factorial structure of the scale of prodromal symptoms. Schizophrenia Research 68:339-347.

Heresco-Levy U, Ermilov M, Lichtenberg P, Bar G, Javitt DC (2004) High-dose glycine added to olanzapine and risperidone for the treatment of schizophrenia. Biological Psychiatry. 55:165-171.

Heresco-Levy U, Ermilov M, Shimoni J, Shapira B, Silipo G, Javitt DC (2002) Placebo-controlled trial of D-cycloserine added to conventional neuroleptics, olanzapine, or risperidone in schizophrenia. American Journal of Psychiatry 159:480-482.

Heresco-Levy U, Javitt DC, Ermilov M, Mordel C, Horowitz A, Kelly D (1996) Double-blind, placebo-controlled, crossover trial of glycine adjuvant therapy for treatment-resistant schizophrenia. British Journal of Psychiatry 169:610-617.

Heresco-Levy U, Javitt DC, Ermilov M, Mordel C, Silipo G, Lichtenstein M (1999) Efficacy of high-dose glycine in the treatment of enduring negative symptoms of schizophrenia. Archives of General Psychiatry 56:29-36.

Ho BC, Andreasen NC, Flaum M, Nopoulos P, Miller D (2000) Untreated initial psychosis: its relation to quality of life and symptom remission in first episode schizophrenia. American Journal of Psychiatry 157:808-815.

Javitt DC (2004b) Glutamate as a therapeutic target in psychiatric disorders. Molecular Psychiatry 9:984-997.

Javitt DC, Balk A, Sershen H, Lajtha A (1999) A.E. Bennett Research Award. Reversal of phencyclidine-induced effects by glycine and glycine transport inhibitors. Biological Psychiatry 45:668-679.

Javitt DC, Silipo G, Cienfuegos A, Shelley AM, Bark N, Park M, Lindenmayer JP, Suckow R, Zulcin SR (2001) Adjunctive high-dose glycine in the treatment of schizophrenia. International Journal of Neuropsychopharmacology 4:385-391.

Javitt DC, Zukin SR (1991) Recent advances in the phencyclidine model of schizophrenia.[see comment]. American Journal of Psychiatry 148:1301-1308.

Jentsch JD, Elsworth JD, Redmond DE, Jr., Roth RH (1997a) Phencyclidine increases forebrain monoamine metabolism in rats and monkeys: modulation by the isomers of Ha.966. Journal of Neuroscience 17:1769-1775.

Jentsch JD, Redmond DE, Jr., Elsworth JD, Taylor JR, Youngren KD, Roth RH (1997b) Enduring cognitive deficits and cortical dopamine dysfunction in monkeys after long-term administration of phencyclidine. Science 277:953-955.

Kapur S, Remington G (2001) Dopamine D(2) receptors and their role in atypical antipsychotic action: still necessary and may even be sufficient. Biological Psychiatry 50:873-883.

Kegeles LS, Abi-Dargham A, Zea-Ponce Y, Rodenhiser-Hill J, Mann JJ, Van Heertum RL, Cooper TB, Carlsson A, Laruelle M (2000) Modulation of amphetamine-induced striatal dopamine release by ketamine in humans: implications for schizophrenia. Biological Psychiatry 48:627-640.

Krystal JH, Karper LP, Seibyl JP, Freeman GK, Delaney R, Bremner JD, Heninger GR, Bowers MB, Jr., Chamey DS (1994) Subanesthetic effects of the noncompetitive Nmda antagonist, ketamine, in humans. Psychotomimetic, perceptual, cognitive, and neuroendocrine responses. Archives of General Psychiatry 51:199-214.

Lahti AC, Holcomb 1111, Medoff DR, Tamminga CA (1995a) Ketamine activates psychosis and alters limbic blood flow in schizophrenia. Neuroreport 6:869-872.

Lahti AC, Koffel B, LaPorte D, Tamminga CA (1995b) Subanesthetic doses of ketamine stimulate psychosis in schizophrenia. Neuropsychopharmacology 13:9-19.

Lahti AC, Weiler MA, Tamara Michaelidis BA, Parwani A, Tamminga CA (2001) Effects of ketamine in normal and schizophrenic volunteers. Neuropsychopharmacology 25:455-467.

LeLorier J, Gregoire G, Benhaddad A, Lapierre J, Derderian F (1997) Discrepancies between meta-analyses and subsequent large randomized, controlled trials. New England Journal of Medicine 337:536-542.

Lencz T, Smith CW, Auther A, Correll CU, Comblatt B (2004) Nonspecific and attenuated negative symptoms in patients at clinical high-risk for schizophrenia. Schizophrenia Research 68:37-48.

Lieberman JA, Perkins D, Belger A, Chakos M, Jarskog F, Boteva K, Gilmore J (2001) The early stages of schizophrenia: speculations on pathogenesis, pathophysiology, and therapeutic approaches. Biological Psychiatry 50:884-897.

Linn GS, O'Keeffe RT, Schroeder CE, T ifshitz K, Javitt DC (1999) Behavioral effects of chronic phencyclidine in monkeys. [erratum appears in Neuroreport Mar. 20, 2000;1 1(4):inside back cover, 901]. Neuroreport 10:2789-2793.

Lu WY, Man HY, Ju W, Trimble WS, MacDonald JF, Wang YT (2001) Activation of synaptic NMDA receptors induces membrane insertion of new AMPA receptors and LTP in cultured hippocampal neurons. Neuron 29:243-254.

Luby ED (1981) Phencyclidine revisited. In Domino EF (ed), PCP (Phencyclidine): Historical and Current Perspectives. Ann Arbor, MI: NPP Books, pp. 25-30.

Malhotra AK, Pinsls DA, Adler CM, Elman I, Clifton A, Pickar D, Breier A (1997) Ketamine-induced exacerbation of psychotic symptoms and cognitive impairment in neuroleptic-free schizophrenics. Neuropsychopharmacology 17:141-150.

Malhotra AK, Pinals DA, Weingartner H, Sirocco K, Missar CD, Pickar D, Breier A (1996) NMDA receptor function and human cognition: the effects of ketamine in healthy volunteers. Neuropsychopharmacology 14:301-307.

Marshall M, Lewis S, Lockwood A, Drake R, Croudace T, Jones P (2003) Systematic review of the association between duration of untreated psychosis and outcome in cohorts of first episode patients (abstract). Schizophrenia Research 70:27.

McGlashan TH (1998) Early detection and intervention of schizophrenia: rationale and research. Br J Psychiatry Suppl 172:3-6.

McGlashan TH, Johannessen JO (1996) Early detection and intervention with schizophrenia: rationale. Schizophrenia Bulletin 22:201-222.

McGlashan TH, Miller TJ, Woods SW (2001) Pre-onset detection and intervention research in schizophrenic psychoses; Current estimates of benefits and risks. Schizophrenia Bulletin 27:563-570.

McGlashan TH, Zipursky RB, Perkins DO, Addington J, Woods SW, Miller TJ, Lindborg S (2004) Olanzapine vs placebo for prodromal schizophrenia. Schizophrenia Research 67:6.

McGorry PD, Yung AR, Phillips U, Yuen HP, Francey S, Cosgrave EM, Germano D, Bravin J, McDonald T, Blair A, Adlard S, Jackson H (2002) Randomized controlled trial of interventions designed to reduce the risk of progression to first episode psychosis in a clinical sample with subthreshold symptoms. Archives of General Psychiatry. 59:921-928.

Miller TJ, McGlashan TI, Rosen JL, Somjee L, Markovitch P, Stein K, Woods SW (2002) Prospective diagnosis of the prodrome for schizophrenia: Preliminary evidence of interrater reliability and predictive validity using operational criteria and a structured interview. American Journal of Psychiatry 159:863-865.

Miller TJ, McGlashan TH, Woods SW, Stein K, Driesen N, Corcoran CM, Hoffman R, Davidson L (1999) Symptom assessment in schizophrenic prodromal states. Psychiatric Quarterly 70:273-287.

Miller TJ, McGlashan TM, Rosen JL, Cadenhead K, Cannon T, Ventura J, McFarlane W, Perkins DO, Pearlson GD, Woods SW (2003a) Prodromal assessment with the Structured Interview for Prodromal Syndromes and the Scale of Prodromal Symptoms: Predictive validity, inter-rater reliability, and training to reliability. Schizophrenia Bulletin 29:703-715.

Miller TJ, Rosen JL, D'Andrea J, Woods SW, McGlashan TH (2004) Outcome of prodromal syndromes: SIPS predictive validity (abstract). Schizophrenia Research 67:44.

Miller TJ, Zipursky RB, Perkins DO, Addington J, Woods SW, Hawkins KA, Hoffman R, Preda A, Epstein I, Addington D, Lindborg S, Tohen M, Breier A, McGlashan TH (2003b) A randomized double blind clinical trial of olanzapine vs placebo in patients at risk for being prodromally symptomatic for psychosis: II. Baseline characteristics of the "prodromal" sample. Schizophrenia Research 61:19-30.

Miyazaki J, Nakanishi S, Jingami H (1999) Expression and characterization of a glycine—binding fragment of the N methyl-D-aspartate receptor subunit NR1. Biochemical Journal 340:687-692.

Moghaddam B, Adams B, Verma A, Daly D (1997) Activation of glutamatergic neurotransmission by ketamine: a novel.step in the pathway from NMDA receptor blockade to dopaminergic and cognitive disruptions associated with the prefrontal cortex. Journal of Neuroscience 17:2921-2927.

Morrison AP, French P, Watford L, Lewis SW, Kilcommons A, Green J, Parker S, Bentall RP (2004) Cognitive therapy for the prevention of psychosis in people at ultra-high risk. Randomized controlled trial. British Journal of Psychiatry 184:291-297.

Mothet JP, Parent AT, Wolosker H, Brady RO, Jr., Linden DJ, Ferris CD, Rogawski MA, Snyder SH (2000) D-serine is an endogenous ligand for the glycine site of the N-methyl-D-aspartate receptor. Proceedings of the National Academy of Sciences of the United States of America 97:4926-4931.

Murray CM, Lopez AD (1996) The Global Burden of Desease: World Health Organization, Harvard University Press.

Nishi M, Hinds H, Lu HP, Kawata M, Hayashi Y (2001) Motoneuron-specific expression of NR3B, a novel NMDA-type glutamate receptor subunit that works in a dominant-negative manner. Journal of Neuroscience 21:1.

Norman RM, Malla AK (2001) Duration of untreated psychosis: a critical examination of the concept and its importance. Psychological Medicine. 31:381-400.

Preda A, Miller TJ, Rosen JL, Somjee L, McGlashan TH, Woods SW (2002) Treatment histories of patients with a syndrome putatively prodromal for schizophrenia. Psychiatric Services 53:342-344.

Robinson DG, Woerner MG, Alvir JMJ, Geisler S, Koreen A, Sheitman B, Chakos M, Mayerhoff D, Bilder R, Goldman R, Lieberman JA (1999) Predictors of treatment response from a first episode of schizophrenia or schizoaffective disorder. American Journal of Psychiatry 156:544-549.

Rosen IL, Woods SW, Miller TJ, McGlashan TH (2002) Prospective observations of emerging psychosis. Journal of Nervous & Mental Disease 190:133-141.

Schell MJ, Molliver ME, Snyder SH (1995) D-serine, an endogenous synaptic modulator: localization to astrocytes and glutamate-stimulated release. Proceedings of the National Academy of Sciences of the United States of America 92:3948-3952.

Stephenson J (1999) Schizophrenia researchers striving for early detection and intervention. JAMA 281:1877-1888.

Sullivan HS (1927) The onset of schizophrenia. American Journal of Psychiatry 7:105-134.

Supplisson S, Bergman C (1997) Control of NMDS Receptor Activation by a Glycine Transporter Co-Expressed in Xenopus aocytes. Journal of Neuroscience 17:4580-4590.

Tsai G, Yang P, Chung LC, Lange N, Coyle IT (1998) D-serine added to anttpsychotics for the treatment of schizophrenia.[see comment]. Biological Psychiatry 44:1081-1089.

Tsai GC, Lane HY, Chang Y -C, Liu Y -C, Chiu C-C (2004a) Sarcosine (N-methylglycine) or D-serine add-on treatment for acute exacerbation of schizophrenia: a randomized, double-blind, placebo-controlled study (abstract). Neuropsychopharmacology 29:S229-230.

Tsai GC, Lane HY, Yang PC, Chong MY, Lange N (2004b) Glycine transporter I inhibitor, N-methylglycine (Sarcosine), added to antipsychotics for the treatment of schizophrenia. Biological Psychiatry 55:452-456.

Tsai GE, Yang P, Chung LC, Tsai IC, Tsai CW, Coyle JT (1999) D-serine added to clozapine for the treatment of schizophrenia. American Journal of Psychiatry 156:1822-1825.

Umbricht D, Schmid L, Koller R, Vollenweider FX Hell D, Javitt DC (2000) Ketamine—induced deficits in auditory and visual context-dependent processing in healthy volunteers: implications for models of cognitive deficits in schizophrenia. Archives of General Psychiatry 57:1139-1147.

Wolosker H, Panizzutti R, DE Miranda J (2002) Neurobiology through the looking-glass: D-serine as a new glial-derived transmitter. Neurochemistry International. 41:327-332.

Woods SW, Breier A, Zipursky RB, Perkins DO, Addington J, Miller TJ, Hawkins K.A., Marquez E, David SR, Tohen M, McGlashan TH (2003) Randomized trial of olanzapine vs placebo in the symptomatic acute treatment of patients meeting criteria for the schizphrenic prodrome. Biological Psychiatry 54:453-464.

Woods SW, Martin A, Spector SG, McGlashan TH (2002) Effects of development on olanzapine-associated adverse events. Journal of the American Academy of Child and Adolescent Psychiatry 41:1439-1446.

Woods SW, McGlashan TH (2002) Sample size planning for prodromal intervention trials (abstract). Schizophrenia Research 53:40.

Woods SW, McGlashan TH (2005) Special issues in intervention: the early phases of schizophrenia. In Sadock BJ, Sadock VA (eds), Comprehensive Textbook of Psychiatry. Baltimore, MD: Lippincott Williams & Wilkins, pp. 1550-1558.

Woods SW, Miller TJ, McGlashan TH (2001) The prodromal patient: Both symptomatic and at risk. CNS Spectrums 6:223-232.

Yang Y, Ge W, Chen Y, Zhang Z, Shen W, Wu C, Poo M, Duan S (2003) Contribution of astrocytes to hippocampal long-term potentiation through release of D-serine. Proceedings of the National Academy of Sciences of the United States of America. 100:15194-15199.

Yung AR, Phillips LT, Yuen HP, Franey SM, McFarlane CA, Hallgren M, McGarry PD (2003) Psychosis prediction: 12-month follow up of a high-risk ("prodromal") group. Schizophrenia Research 60:21-32.

McGorry P (1998) Verging on reality. Br J Psychiatry Suppl 172:1-136.

Javitt, DC, "Glycine modulators in schizophrenia", Current Opinión in Investigational Drugs (2009) vol. 3 , pp. 1067-1072.

Heresco-Levy, U., "N-Methyl-D-aspartate (NMDA) receptor-based treatment approaches in schizophrenia: the first decade", International Journal of Neuropsychopharmacology (2003), vol. 3, pp. 243-258.

Tsai, G., et al., "Glycine Transporter I Inhibitor, N-Methylglycine (Sarcosine), Added to Antipsychotics for the Treatment of Schizophrenia" , Biological Psychiatry (2004), vol. 55, pp. 452-456.

Heresco-Levy, U., et al., "Efficacy of High-Dose Glycine in the Treatment of Enduring Negative Symptoms of Schizophrenia", Archives of General Psychiatry (1999), vol. 56, pp. 29-36.

* cited by examiner

Gliatech (WO0222581) 9

10
NPS Allelix (US2002426364)

11
NPS Allelix (US2002169197)

12
Pfizer EP1284257

13
Lundbeck (WO03053942)

14
Lundbeck (WO04096761)

15
Yamanouchi Merck Patent (WO03031435)

16
Yamanouchi Merck Patent (DE10315570)

17
Smithkline Beecham WO03055478

18
Glaxo Group WO04113280

19
Glaxo Group WO04112787

20
Glaxo Group WO04113301

21
Glaxo Group WO05049023

22
Sanofi-Synthelabo WO03089411

23
Sanofi-Synthelabo WO04013100

24
Sanofi-Synthelabo WO04013101

25
Sanofi-Aventis WO05037783

26
Sanofi-Aventis WO05037792

27
Sanofi-Synthelabo WO04013100

28
Sanofi-Aventis WO05037781

Glaxo Group
39 WO05058317

Merck & Co.
40 WO05046601

Merck Patent
WO03087086
41

Merck Patent
WO03076420
42

43
NPS Allelix
WO040022528

METHOD OF TREATING SCHIZOPHRENIA PRODROME

This application claims priority from U.S. provisional application Ser. No. US60/670,600, filed Apr. 11, 2005, which is incorporated by reference in its entirety herein.

FIELD OF THE INVENTION

The present invention relates to a method of treating schizophrenia prodrome in human subjects using an NMDA glycine site agonist, a glycine transporter-1 inhibitor or mixtures thereof, optionally in combination with a pharmaceutically acceptable additive, carrier or excipient.

BACKGROUND OF THE INVENTION

Schizophrenia is a common, debilitating, sometimes life-threatening illness. In the 1990 World Health Organization ranking of public health burden in developed regions (Murray and Lopez, 1996), schizophrenia lay ahead of diabetes, cirrhosis, drug use, breast cancer, asthma, rheumatoid arthritis, and HIV. Currently available treatments for schizophrenia include both conventional antipsychotics, which were first developed in the late 1950s, as well as new generation atypical antipsychotics, which have been developed over the past decade. Despite recent advances in treatment including the new generation medications, most schizophrenic patients continue to remain chronically disabled. Because the disorder typically arises in adolescents and young adults, the resulting chronicity too often is life long.

Schizophrenia Prodrome—Need for New Treatments

Although schizophrenia is heterogenous, most patients may be characterized as following a course consisting of premorbid, prodromal, and psychotic illness phases (Woods and McGlashan, 2005). The premorbid phase describes an asymptomatic period of normality or relatively subtle and stable impairments starting from birth. The prodromal phase is conceptualized as the first symptomatic phase, and is shorter in duration and escalating in severity. When patients become fully psychotic they are defined as having experienced the onset of schizophrenia as we currently conceptualize it. Current treatment guidelines apply only to the frankly psychotic phase of illness post onset.

The prodromal phase of schizophrenic disorders has been recognized since the $19^{th}$ century (Bleuler, 1911). The possibility of treatment intervention during the prodromal phase has a history almost as long (Sullivan, 1927). A recent strong resurgent interest in this area (McGlashan, 1998; McGlashan and Johannessen, 1996; McGorry, 1998; Stephenson, 1999) stems largely from two developments.

First, neurobiological deficit processes associated with the severity and chronicity of schizophrenia have been demonstrated already to be present by the time onset is recognized (McGlashan and Johannessen, 1996). Thus these deficit processes begin before onset of illness as we currently define it. Intervention during the prodrome offers hope of influencing these processes earlier in their development.

Second, most (see (Lieberman et al., 2001; Norman and Malla, 2001; Woods et al., 2001) for reviews) although not all (Barnes et al., 2000; Chen et al., 1999; Craig et al., 2000; Ho et al., 2000; Robinson et al., 1999)) studies with antipsychotic medication suggest that treatment earlier in the active phase may be associated with better long term outcome than delayed application of the same treatment. Max Marshall (Marshall et al., 2003) and Jeff Lieberman (personal communication) have each conducted formal meta-analyses to this literature, each of which reveal a strong positive overall effect of earlier treatment. These results suggest that intervention earlier in the course of illness, before the active phase, may be associated with even better long-term outcome. Prevention of the chronic disability of schizophrenia could even be envisioned.

Substantial progress has been made in recent years in addressing the accuracy of patient identification during the prodromal phase. Our group has elaborated criteria and a structured interview for diagnosing the prodromal phase (the Structured Interview for Prodromal Syndromes (SIPS) (Woods et al., 2001)). The criteria are based on subthreshold levels of positive symptoms of schizophrenia such as attenuated delusions (unusual thought content) and attenuated hallucinations (perceptual abnormalities). We have shown that reliability of the prodromal diagnosis is excellent (Miller et al., 2002; Miller et al., 2003a) and that prodromal patients are highly symptomatic (Miller et al., 2003b; Woods et al., 2001), functionally impaired (McGlashan et al., 2001; Miller et al., 2003b), cognitively impaired (Hawkins et al., 2004a), and treatment-seeking (Preda et al., 2002). In addition, these patients are at risk for schizophrenia. Onset risk in 12 months was 54% in our without treatment sample (Miller et al., 2002) and 47% in second sample randomized to placebo (Miller et al., 2004). Onset risk has been similar, about 30-50% in the next year, in other sites around the world that use similar criteria (Morrison et al., 2004; Yung et al., 2003). Taken together, we believe this evidence indicates that these patients constitute a new clinical population in need of effective treatment and definition of a standard of care.

Only three studies thus far have addressed treatment needs of prodromal patients. The first two studied antipsychotic medication. A recently completed trial randomized 59 patients to open-label risperidone plus cognitive therapy plus usual care versus usual care alone (McGorry et al., 2002). Six month conversion to psychosis rates were 9.7% for the risperidone containing treatment and 35.7% for usual care (p<0.05). Our group has completed a 12 month trial randomizing 60 patients to olanzapine vs placebo (McGlashan et al., 2004; Woods et al., 2003). Twelve month conversion rates were 16% for olanzapine and 38% for placebo, a statistically significant difference when controlling for baseline severity imbalance. The third study randomized 58 prodromal patients to cognitive therapy vs monitoring (Morrison et al., 2004). Cognitive therapy group showed significantly lower rates when two patients later believed to have been already psychotic were excluded.

Prodromal research studies thus far have focused primarily on the aim of preventing the development of schizophrenic psychosis. While this is certainly an important goal, ethical issues are raised because some patients will be false positives who have no personal opportunity to benefit if benefit is defined solely as prevention. Prodromal patients are highly symptomatic, yet little attention has thus far been paid to determining whether treatment improves the patients' current symptoms. Focusing on symptomatic improvement lessens ethical concerns because each patient enrolled will personally have prospect of benefit to balance off against risk (Woods et al., 2001). Our group conducted such analyses over the short term in its olanzapine vs placebo trial, using the SOPS as the primary outcome measure (Woods et at., 2003). The results showed that prodromal symptoms improved significantly more with placebo than with olanzapine. Prodromal patients changed little with placebo.

NMDA Hypofunction—A Novel Neurobiologic Target for Treatment in the Schizophrenia Prodrome Antipsychotic medications were tried first for prodromal patients. A part of the concern about prodromal intervention is that even the new atypical antipsychotics can have worrisome side effects, including weight gain and metabolic syndrome. Many of these side effects can be more prominent in adolescents than in adults (Woods et al., 2002). Although it makes sense that antipsychotic medications would be tried first for prodromal patients, the prodrome may involve neurotoxic or degenerative processes that are distinct from the neurobiology associated with the chronic stages of schizophrenia. Other medications, perhaps only weakly effective for chronic patients, could influence the potentially unique neurobiology of the prodromal phase and might thereby improve prodromal symptoms and/or prevent schizophrenia from developing.

There are numerous examples throughout medicine where the same treatment can be fully effective and even curative when given early in the course of illness and yet less effective or even completely ineffective later in the course of illness after the pathophysiology has changed. One familiar example is neonatal hypothyroidism (cretinism). This condition is asymptomatic at birth because the fetus has developed normally due to access to maternal thyroid hormone. If the illness is detected by screening shortly after birth, early thyroid hormone supplementation allows fully normal postnatal neurologic development. However, if the illness is not detected until neurologic symptoms develop, later thyroid hormone supplementation corrects thyroid hormone levels but does not restore normal neurologic functioning, and the child remains chronically developmentally disabled.

All currently approved treatments for schizophrenia, including both typical and atypical antipsychotics, were developed based upon dopaminergic theories of schizophrenia and function primarily by blocking neurotransmission at D2-type dopamine receptors, with interactions at other receptors producing only a portion of the variability in clinical effectiveness between agents (Kapur and Remington, 2001). These were also the first agents to be tested for the schizophrenia prodrome (McGorry et al., 2002; Woods et al., 2003). The novel treatment proposed for the schizophrenia prodrome in this patent application is based upon an alternative, glutamatergic or NMDA hypofunction model of schizophrenia and its prodrome (see below).

Direct or Indirect NMDA/Glycine-Site Agonists

Agents that Target NMDA Hypofunction in the Schizophrenia Prodrome

The NMDA Hypofunction Model of Schizophrenia. Traditional models of schizophrenia have focused primarily upon the role of dopamine. Dopamine models are based on two primary lines of evidence: first, the ability of amphetamine and other dopamine releasing agents to stimulate psychosis that closely resembles schizophrenia, especially following chronic use, and, second, the ability of agents that block dopamine (D2) receptors to reverse certain symptoms. Symptoms of schizophrenia are traditionally divided into 3 symptom clusters: a positive cluster consisting of symptoms such as agitation, paranoia and paranoid delusions; a negative cluster consisting of symptoms such as motor retardation, emotional withdrawal and passive/apathetic social withdrawal; and a cognitive (AKA autistic or disorganized) cluster consisting of symptoms such as disorientation or conceptual disorganization. A limitation of the dopamine model is that amphetamine induces symptoms resembling primarily the positive symptoms of schizophrenia, but does not induce symptoms resembling either the negative or cognitive symptoms. Further, antipsychotics have proven far more effective as a group, in treatment of positive, than negative symptoms of schizophrenia.

Glutamatergic models were first developed starting in the late 1950's based upon the observation that phencyclidine (PCP), ketamine and related psychotomimetic compounds induced symptoms in normal volunteers that closely resembled both the positive and negative symptoms of schizophrenia (Domino and Luby, 1981; Luby, 1981). Subsequent investigation demonstrated that these compounds functioned by blocking neurotransmission at NMDA-type glutamate receptors, leading to the hypothesis that endogenous dysfunction or dysregulation of NMDA receptor-mediated neurotransmission might contribute substantially to the pathophysiology of schizophrenia (Abi-Saab et al., 1998; Coyle and Tsai, 2004; Javitt and Zukin, 1991).

Since the discovery of the unique behavioral effects of PCP, a number of studies have been performed to evaluate the degree of similarity between the symptoms and neurocognitive deficits induced by NMDA antagonists and those observed endogenously in schizophrenia Studies were conducted first using PCP itself until the drug was withdrawn from the market in the late 1960s. In those studies, PCP was found to induce not only symptoms, but also neuropsychological deficits that closely resemble those of schizophrenia (Domino and Luby, 1981). More recent studies with ketamine strongly support and extend the initial observations. Thus, for example, ketamine infusion has been shown to induced deficits in Wisconsin Card Sorting (Krystal et al., 1994) and AX-type Continuous Performance (Umbricht et al., 2000) test performance that closely resembles the pattern observed in schizophrenia Similarly, ketamine induces transient memory deficits (Malhotra et al., 1996) and thought disorder (Adler et al., 1998) similar to those in schizophrenia, and exacerbates psychotic symptoms in patients with schizophrenia (Lahti et al., 1995b; Lahti et al., 2001; Malhotra et al., 1997). Further, ketamine reproduces both sensory-level disturbances, as measured using event-related potentials such as mismatch negativity (MMN) (Umbricht et al., 2000), as well as causing schizophrenia-like alterations in frontotemporal blood flow (Lahti et al., 1995a). In PET studies, ketamine both stimulates dopamine release in regions such as striatum (Breier et al., 1998), and potentiates effects of amphetamine as observed in schizophrenia (Kegeles et al., 2000). In an fMRI study, ketamine produced reduced fMRI activations during target detection in anterior cingulate cortex (ACC) and dorsolateral prefrontal cortex (DLPFC) in healthy subjects (Belger et al., in preparation) similar to those reported in schizophrenia.

BRIEF DESCRIPTION OF THE INVENTION

Figure 1A:
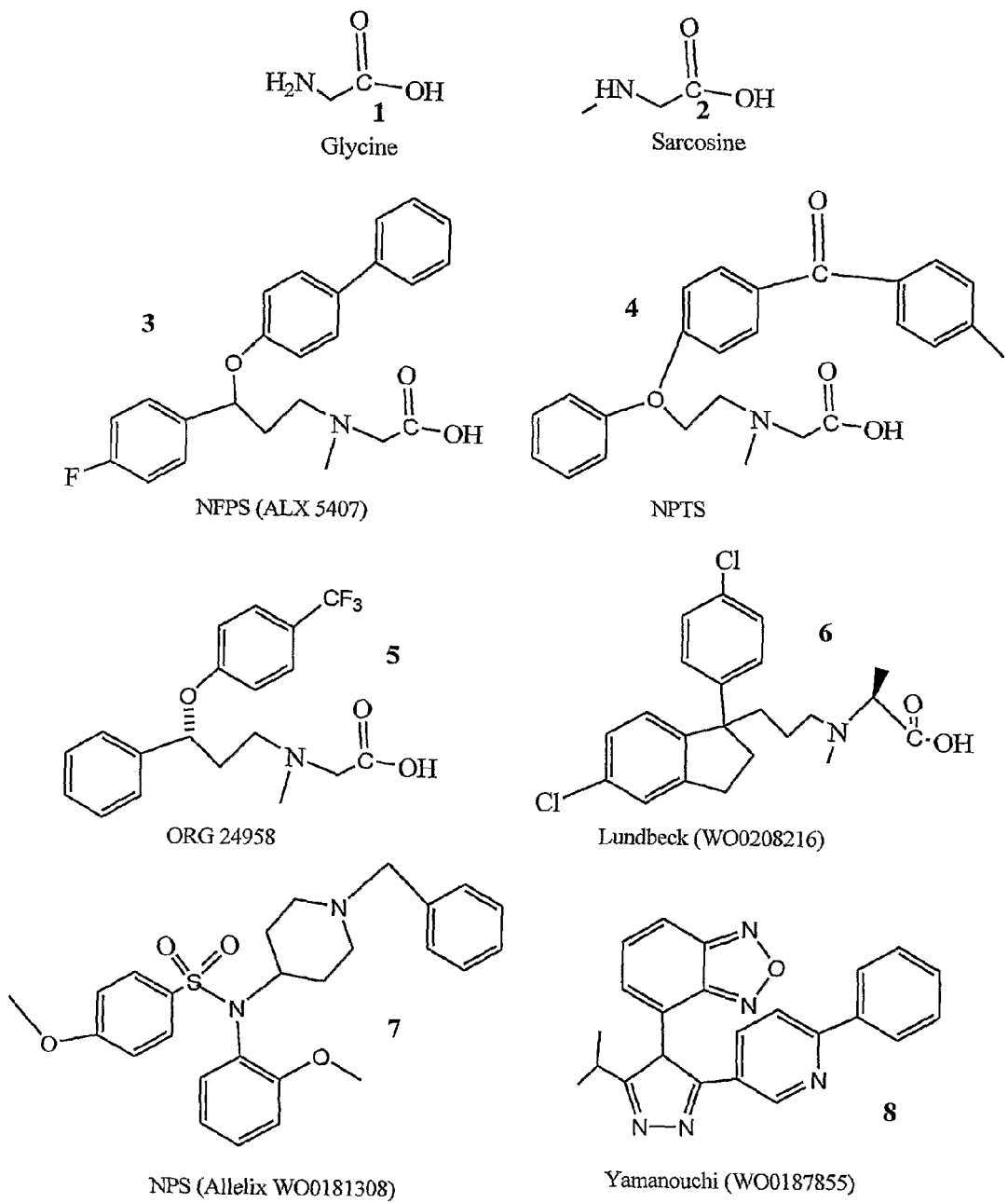
FIGS. 1A-E depicts a number of compounds (43), which are primarily glycine transporter-1 inhibitors (compounds 2-43) and can be used to treat prodromal schizophrenia in the present application.
Figure 1B:
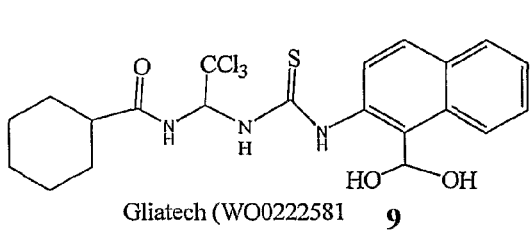
Figure 1B:
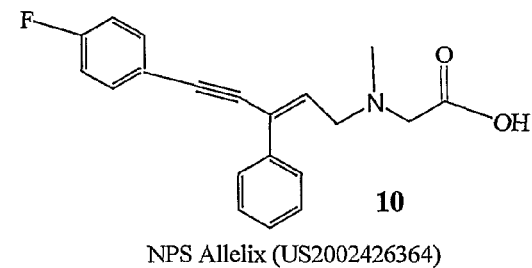
Figure 1B:
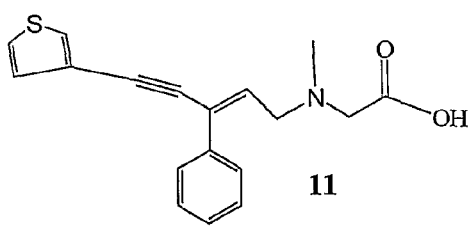
Figure 1B:
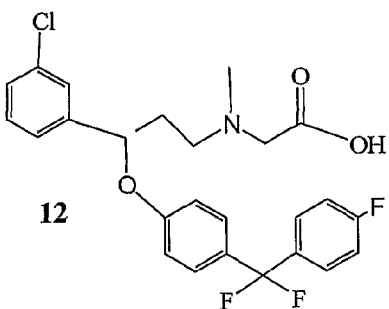
Figure 1B:
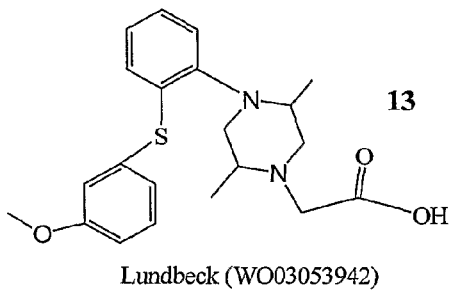
Figure 1B:
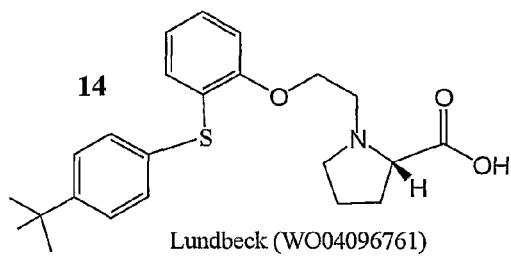
Figure 1B:
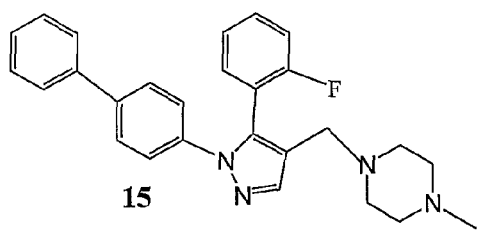
Figure 1B:
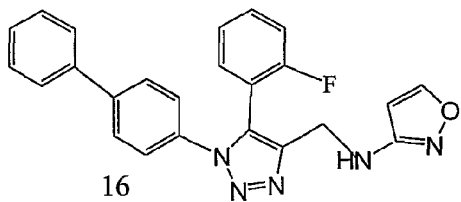
Figure 1B:
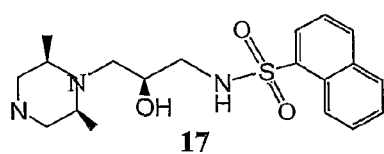
Figure 1B:
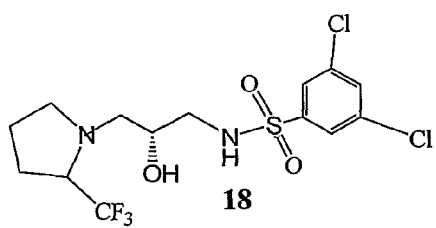
Figure 1C:
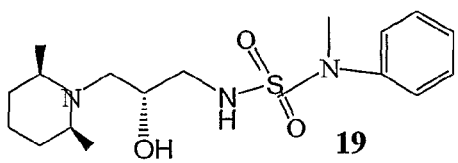
Figure 1C:
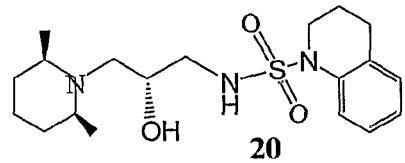
Figure 1C:
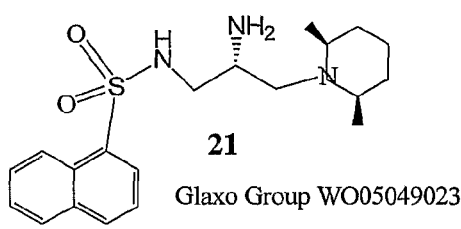
Figure 1C:
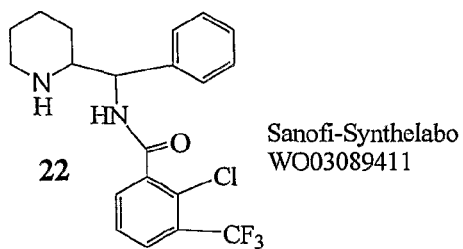
Figure 1C:
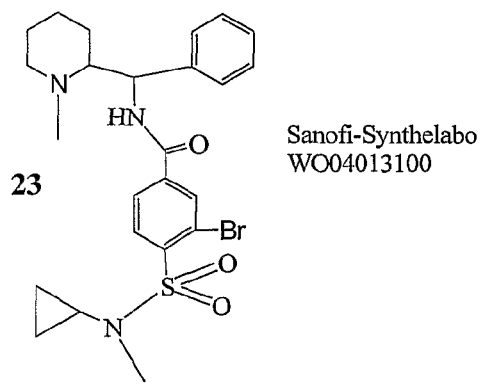
Figure 1C:
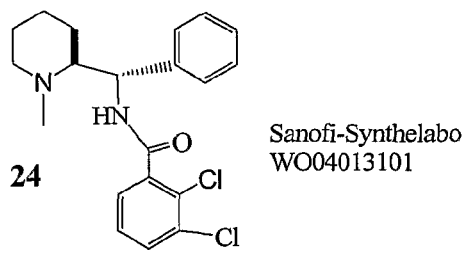
Figure 1C:
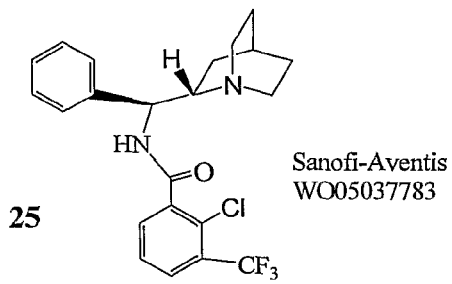
Figure 1C:
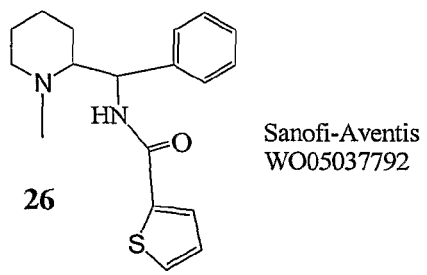
Figure 1C:
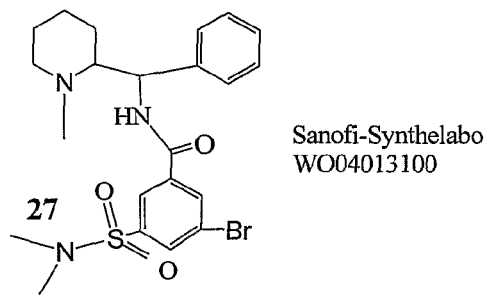
Figure 1C:
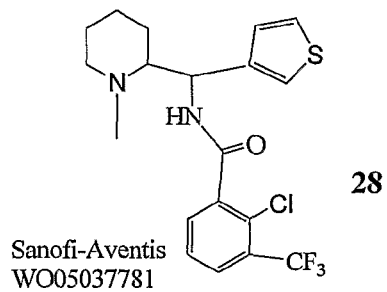
Figure 1D:
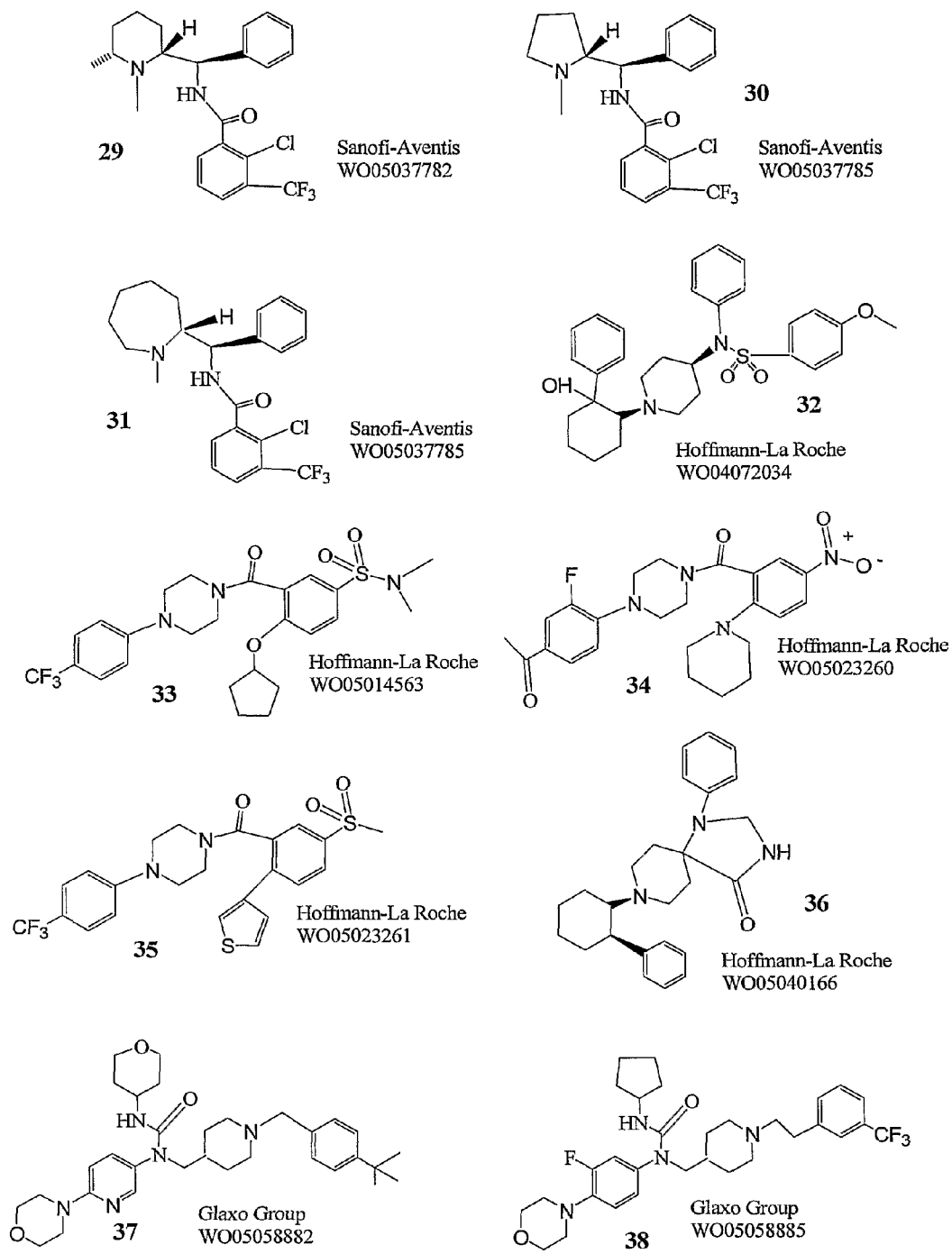
Figure 1E:
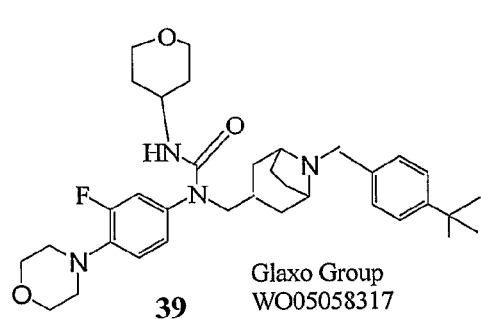
Figure 1E:
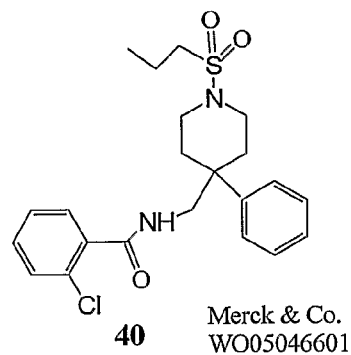
Figure 1E:
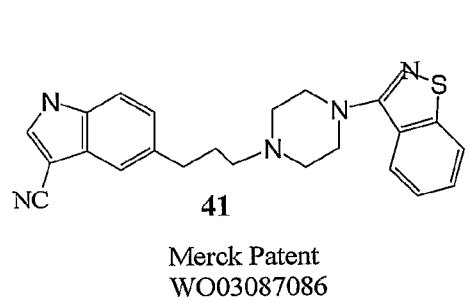
Figure 1E:
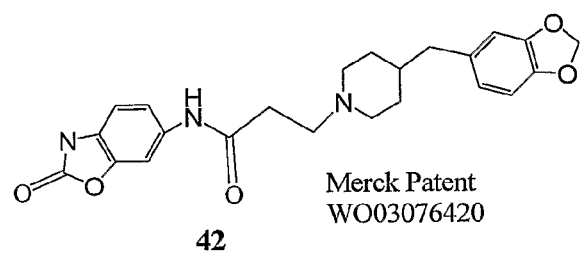
Figure 1E:
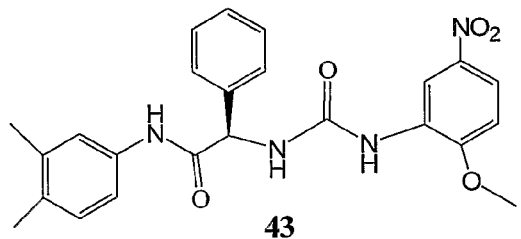

The present invention relates to the use of a NMDA/glycine site agonist and/or a glycine transporter inhibitor to treat prodromal schizophrenia in a patient. In this method of the present invention, a patient or subject exhibiting symptoms of prodromal schizophrenia (initial or relapse prodrome) is administered an effective amount of a compound selected from the group consisting of a NMDA/glycine site agonist, a glycine transporter inhibitor or mixtures thereof, optionally in combination with a pharmaceutically acceptable carrier, additive or excipient, in order to treat the symptoms of prodromal schizophrenia (reduce the severity of and/or eliminate one or more, preferably a majority and more preferably virtually all symptoms of prodromal schizophrenia) or prevent or substantially reduce the likelihood that the patient's prodromal schizophrenia will become frank psychosis.

In particular aspects of the invention, a NMDA glycine site agonist according to the structure is an amino acid or related derivative according to the chemical structure:

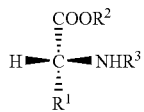

Where $R^1$ is H, $CH_3$ or $CH_2OR^4$;

$R^2$ is H or a $C_1$-$C_{20}$ optionally substituted alkyl group;

$R^3$ is H, or a $C_2$-$C_{21}$ optionally substituted acyl group; and $R^4$ is H or a $C_2$-$C_{21}$ optionally substituted alkyl group, or a pharmaceutically acceptable salt, solvate (including a hydrate) or polymorph thereof is administered alone or preferably in combination with a pharmaceutically acceptable carrier, additive or excipient and optionally in combination with a glycine transporter inhibitor to a patient or subject exhibiting symptoms of prodromal schizophrenia in order to treat said symptoms of prodromal schizophrenia and/or preferably to prevent or at least reduce the likelihood that the patient's prodromal schizophrenia will progress to frank psychosis.

In other aspects of the invention, the method comprises administering an effective amount of a glycine transporter inhibitor (such as sarcosine or a derivative as presented below or any of the compounds 3-43 set forth in FIGS. 1-5 hereof) or a pharmaceutically acceptable salt, solvate (including a hydrate) or polymorph thereof to said patient exhibiting symptoms of prodromal schizophrenia in order to treat said symptoms of prodromal schizophrenia and/or preferably to prevent or at least reduce the likelihood that the patient's prodromal Preferred glycine transporter inhibitors include sarcosine and derivative compounds according to the chemical structure:

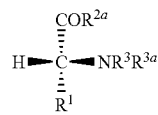

Where $R^1$ is H or $CH_3$;

$R^{2a}$ is OH, a $C_1$-$C_{20}$ optionally substituted alkoxy group (forming the ester), an optionally substituted $C_1$-$C_{20}$ hydrocarbyl group or an optionally substituted heterocyclic or heteroaromatic group;

$R^{3a}$ is $CH_3$ or together with $R^3$ or $R^1$ forms an optionally substituted heterocyclic or heteroaromatic group; and $R^3$ is H, a $C_2$-$C_{21}$ optionally substituted acyl group, or an optionally substituted $C_1$-$C_{20}$ (preferably an optionally substituted $C_5$-$C_{20}$) hydrocarbyl group, or an optionally substituted heterocyclic or heteroaromatic group, or a pharmaceutically acceptable salt, solvate (including a hydrate) or polymorph thereof is administered alone or preferably in combination with a pharmaceutically acceptable carrier, additive or excipient and optionally in combination with a NMDA glycine site agonist (as described above) to a patient or subject exhibiting symptoms of prodromal schizophrenia in order to treat said symptoms of prodromal schizophrenia and/or preferably to prevent or at least reduce the likelihood that the patient's prodromal schizophrenia will progress to frank psychosis.

Especially preferred compounds for use in the present invention include the compounds which are presented as compounds 2-43 in attached FIGS. 1A-E.

DETAILED DESCRIPTION OF THE INVENTION

The term "patient" or "subject" is used throughout the specification to describe a subject preferably a human, to whom treatment, including prophylactic treatment, with the compounds/compositions according to the present invention is provided. In general, the treatment is for human patients or subjects unless otherwise specified.

The term "compound", as used herein, unless otherwise indicated, refers to any specific chemical compound disclosed herein and includes in context, tautomers, regioisomers, geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds.

The term "independently" is used herein to indicate that the variable, which is independently applied, varies independently from application to application.

The term "hydrocarbyl" shall mean within its use in context, a radical containing carbon and hydrogen atoms, preferably containing between 1 and 20 carbon atoms. Such term may also include cyclic groups and unsaturated groups such as aromatic groups, within context. A substituted hydrocarbyl group is a hydrocarbyl group where at least one hydrogen atom is substituted by another moiety, as described below. The term "alkyl" shall mean within its use in context a fully saturated $C_1$-$C_{12}$ hydrocarbon linear, branch-chained or cyclic radical, preferably a $C_1$-$C_4$, even more preferably a $C_1$-$C_3$ linear, branch-chained or cyclic fully saturated hydrocarbon radical. The term "alkenyl" is used to describe a hydrocarbon group, similar to an alkyl group which contains one double bond. Unsaturated hydrocarbyl groups, including acetylenic groups, are anticipated for use in the present invention. The terms "alkylene" and "alkenylene" may be used to describe alkyl and alkenyl divalent radicals generally of up to about 12 carbon units in length and preferably no greater than about 6 carbon units per length (for example, 1-4 carbon units in length) and may be subsumed under the terms alkyl and alkenyl, especially when referring to substituents or substituted.

The term "aromatic" or "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include optionally substituted heterocyclic aromatic ring groups ("heteroaromatic" or "heteroaryl") having one or more nitrogen, oxygen, or sulfur atoms in the ring, such as imidazolyl, furyl, pyrrolyl, pyridyl, thiophene, thiazole, indolyl, quinoline, among numerous others. The preferred aryl group in compounds according to the present invention is a phenyl or a substituted phenyl group, including a biphenyl group.

The term "heterocycle" shall mean an optionally substituted moiety which is cyclic and contains at least one atom other than a carbon atom, such as a nitrogen, sulfur, oxygen or other atom. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated (heteroaromatic).

The term "unsubstituted" shall mean substituted only with hydrogen atoms. The term "substituted" shall mean, within the chemical context of the compound defined, a substituent (each of which substituent may itself be substituted) selected from a hydrocarbyl (preferably, up to 12 carbon units in size, which may be substituted itself, saturated or unsaturated, preferably with an optionally substituted alkyl or fluoro group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen, thiol or ($=$S), hydroxyl, carboxyl, oxygen (to form a keto group), $C_1$-$C_8$ alkoxy, CN, nitro, an optionally substituted amine (e.g. an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ thioether, amide (amido or carboxamido), substituted amide (especially mono- or di-alkylamide) or alkyleneamine, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "pharmaceutically acceptable salt" is used throughout the specification to describe a salt form of analogs of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Additional salts include acid addition salts of amines such as, for example, HCl salts, carboxylic acid salts (malate, citratre, taurate, oxalate, etc.) and phosphate salts, among numerous others. Salt formulation is a function of the chemical formula of a given compound, as one of ordinary skill will readily understand.

The term "effective amount" shall mean an amount or concentration of a compound or composition according to the present invention which is effective within the context of its administration, which may be inhibitory, prophylactic and/or therapeutic. Compounds according to the present invention are particularly useful for providing favorable change in the disease or condition/symptoms treated, whether that change is an effect of the condition or disease to be treated, a favorable physiological result or a reduction in symptomology associated with the disease or condition treated. The term "effective amount" also subsumes temporal and durational considerations of administration under the general rubric.

The term "pharmaceutically acceptable carrier" refers to a carrier, additive or excipient which is not unacceptably toxic to the subject to which it is administered. Pharmaceutically acceptable excipients are described at length by E. W. Martin, in "Remington's Pharmaceutical Sciences", among other references well-known in the art.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "coadministration" or "combination therapy" is used to describe a therapy in which at least two active compounds in effective amounts are used to treat prodromal schizophrenia at the same time. Although the term coadministration preferably includes the administration of two active compounds to the patient at the same time, it is not necessary that the compounds be administered to the patient at the same time, although effective amounts of the individual compounds will be present in the patient at the same time.

The term "prodromal schizophrenia" is used to describe a condition which is a forerunner of schizophrenia as a psychotic disorder. The term "prodrome" is derived from the Greek word prodromos meaning the forerunner of an event. In clinical medicine, a prodrome refers to the early symptoms and signs of an illness that precede the characteristic manifestations of the acute, fully developed illness. For example, measles is described as having a prodrome of 3 to 4 days characterized by fever, coryzal symptoms, conjunctivitis, and cough. This is followed by the specific rash, making definitive diagnosis possible. Prodrome in psychotic disorders is similarly defined. This may be described as a heterogeneous group of behaviors temporally related to the onset of psychosis or the time interval from onset of unusual behavioral symptoms to onset of psychotic symptoms. Alternatively, it may be defined as the period from first noticeable symptoms to first prominent psychotic symptoms. Regardless of description, the term refers to a period of prepsychotic disturbance, representing a deviation from a person's previous experience and behavior which often results in a psychotic condition. If the prodrome concept is restricted to its retrospective meaning, diagnosed only after the development of definitive symptoms and signs, opportunities for early intervention are lost.

The term "prodrome" has been used prospectively by some authors to denote the prepsychotic period before the first onset of a psychotic illness or first psychiatric intervention. It is also referred to as an "initial prodrome" in contrast to "relapse prodrome" which presages a relapse of pre-existing franc psychosis. In the present application, the term "prodrome" or "prodromal" is used in context to describe the invention instead of the longer "initial prodrome." The present invention does not relate to the treatment of relapse prodrome. In the present invention, a patient is in prodrome (initial or relapse) when the patient meets prodrome diagnostic criteria, attenuated positive symptom subgroup, according to the Structured Interview for Prodromal Syndromes (Miller et al., 2002).

Initial prodrome is defined as the period of time from the first noticeable change in a person until development of the first frank psychotic symptoms. There are some difficulties with accurately defining this period of time. This period is defined by symptomology recognized by patients, family members or others in regular contact with the patient and the severity of symptoms or change in functioning of a hypothetical patient who has developed a psychosis and then recovered. The prodrome (initial and/or relapse) includes a condition when the patient first noticed some change (generally psychological in nature) in himself/herself, but not symptoms that would be called psychotic. For example, he/she may have noticed that he was not coping with stress as well as he usually would or may have noticed vague depressive feelings or uneasiness; he may remember difficulties focusing his attention. Changes may have been subtle, so that only the patient and not his acquaintances noticed.

In addition to the patient recognizing some mental (cognitive), psychological, physical or behavioral change, the prodrome also includes the point when the patient's family or friends noticed some such change in the person, but not changes which are indicative of frank psychosis. They may have put it down to "a phase he was going through" (particularly in the case of adolescents) or thought it was worries at work. As the prodrome progresses, new symptoms emerge to the point when the patient first noticed changes that would be described as psychotic, but not sufficiently severe to indicate frank psychosis. For example, he might describe hearing "sounds" (as opposed to hearing voices in frank psychosis) or having had the belief that others were attempting to influence him (as opposed to external agencies controlling his mind in frank psychosis.

The prodrome ends with the patient experiencing symptoms of frank psychosis and the clear-cut necessity to seek psychiatric intervention/help to manage or with the first psychiatric intervention, such as community team involvement or admission into a hospital. The symptom severity then decreases following effective intervention.

The following symptoms have been associated with initial prodrome.
Neurotic Symptoms
Anxiety
Restlessness
Anger, irritability
Mood Related Symptoms
Anhedonia
Depressed mood
Guilt
Suicidal
Mood swings
Changes in Volition
Apathy, loss of drive
Boredom, loss of interest
Fatigue, loss of energy
Cognitive Changes
Disturbances of Attention—inability to concentrate
Preoccupation—daydreaming
Thought blocking
Reduced abstraction
Physical Symptoms
Somatic complaints
Poor appetite
Sleep disturbances
Other Symptoms
Obsessive Compulsive Phenomena
Dissociative Phenomena
Increased Interpersonal Sensitivity
Change in sense of self, others or the world
Speech Abnormalities
Subsyndromal perceptual abnormalities
Suspiciousness
Other subsyndromal unusual thought content
Change in affect
Behavioral Changes
Deterioration in school work or other role functioning
Social withdrawal
Impulsivity
Odd Behavior
Aggressive or Disruptive Behavior In addition to the symptoms which are described above, the patterns of changes in the symptoms are also important. Thus, in addition to the range of subjective symptoms and observable behavioral changes in the schizophrenic prodrome, the sequence of such changes over time is also important. The prodrome is a process, involving changes in experiences and behavior over time, rather than a simple list of symptoms at any one point. The prodrome is a moment to moment march of psychological changes. There are two schools of thoughts regarding the sequence of changes in symptoms which represents a prodrome which has a high probably of leading to psychosis and is treated according to the present invention.

Pattern 1: Nonspecific changes, followed by specific prepsychotic symptoms, then psychosis.

One school of thought considers the prodrome to consist of nonspecific neurotic-type symptoms, followed by more marked deviations from normal, eventually leading to frank psychosis. Subjective symptoms are usually accompanied by some deterioration in role functioning and other behavioral changes. Two patterns of nonspecific changes in the schizophrenic prodrome: "changes of hypofunction" and "changes of hyperfunction." The hypofunction pattern is characterized by seclusive, quiet, and withdrawn behavior. The hyperfunction pattern is characterized by complaints of nervousness, restlessness, tenseness, unease, apprehension, and anxiety. These nonspecific symptoms may last weeks to years before the onset of the "specific" symptoms heralding impending psychosis. These are symptoms of a clinically recognizable schizophrenic nature" (p. 569) and consist of suspiciousness, feelings that their external environment had lost its feeling of familiarity, and feeling "dazed" or "confused". These symptoms would seem to be attenuated forms of frank psychotic phenomena. It is believed that the early specific changes often persisted for months to years before the person came to the attention of psychiatric services.

Pattern 2: Early specific changes, with neurotic symptoms as a reaction to these, then psychosis. An alternative view on the pattern of changes is that specific subjective changes occur first and are followed by apparent neurotic symptoms and behavioral change. This phenomenon comprises the following:

1. Disturbances in attention. This is a fundamental symptom in early schizophrenia and the underlying mechanism for some subsequent symptoms and behaviors. The chief abnormality in attention is the inability to filter out irrelevant stimuli, a disturbance of the ability to selectively attend to information. The patient is distracted by multiple events and feels overwhelmed, resulting in information overload and finally a total disruption in attention.

2. Disturbances in perception. These are described as intermittent, transient, but occasionally severe. Included are abnormalities in visual perception, such as seeing objects as altered in size, shape, color, brightness, movement, and distance away from the observer. Also included are the patient's inability in some cases to perceive objects as a whole, being diverted to inspecting parts of the whole instead, resulting in an inability to see the overall "Gestalt" of the image—which relates back to the disorder of selective attention.

3. Blocking phenomena. This term refers to sudden disruptions in attention, thought, perception, memory, speech, and motility. The patient is aware of intermittent "blank spells" or "trances". These blocking phenomena may be caused by defects in selective attention. As the patient becomes more and more distracted by multiple sensory experiences, he would then switch suddenly to being unable to attend at all. With increasing volumes of information that he is unable to process, the patient finally reaches a point where his consciousness is disturbed.

4. Disturbances in speech production. These are described as intermittent and include disturbances in the production of speech as well as in the ability to understand speech. They are secondary to a disorder of selective attention.

5. Disturbances in motor function. This includes loss of spontaneous movements and coordination. Disorders of motility are secondary to disturbances of both attention and perception, for example, having to stop moving because of certain visual or auditory sensations. Motility and perceptions are intimately linked, motility being dependent upon the stability of the perceptual field.

Thus, in prodrome schizophrenia, patients may experience relatively subtle disturbances of attention, perception, thought, speech, and motility subjectively before signs of established disease appear overtly and long before the patient actually complains to others of symptoms. The prodrome may include almost every kind of neurotic symptom. Anxiety is most common and depression is also common. These neurotic symptoms generally follow subjective changes and were but superficial indications of disturbance in the patient, essentially reactions to the underlying primary disturbances of attention and perception. As the prodrome progresses toward schizophrenia, more specific symptoms emerge, such as the attenuated or subsyndromal subtle hallucinatory or predelusional experiences described above. Many delusions may similarly arise from pre-existing disturbances in cognition and perception and serve as a way for patients to explain the phenomena they are experiencing.

NMDA Hypofunction Hypothesis in the Schizophrenia Prodrome. As discussed above, the earliest signs of schizophrenia during the "premorbid" phase (Woods and McGlashan, 2005) consist primarily of negative symptoms, disordered or illogical thinking, and cognitive decline. These may predate development of frank psychotic symptoms by months to years (Hafner et al., 1993). Negative symptoms and cognitive dysfunction remain troublesome a bit later in the course of illness when patients are diagnosable as prodromal (Cornblatt et al., 2003; Hawkins et al., 2004a; Lencz et al., 2004; Miller et al., 2003b). The NMDA hypofunction model accounts for negative symptoms and cognitive dysfunction to a far greater degree than the dopamine model (Abi-Saab et al., 1998; Coyle and Tsai, 2004; Javitt and Zukin, 1991).

One key divergence between ketamine-induced psychosis and schizophrenia is the relative absence of auditory hallucinations during ketamine administration to normal volunteers. In contrast, in patients with established schizophrenia, exacerbation of hallucinations as well as other features of psychosis is observed (Lahti et al., 1995b; Lahti et al., 2001; Malhotra et al., 1997). The reason for this discrepancy is unclear, but may reflect the natural history of schizophrenia. During the prodromal phase, fully-formed schizophrenia-like auditory hallucinations are absent, although patients often experience vague auditory distortions or illusions (Miller et al., 1999; Miller et al., 2003b; Rosen et al., 2002). Challenge studies with NMDA antagonists are necessarily brief and thus may be viewed as reproducing in healthy volunteers only the earliest symptoms of schizophrenia. These considerations suggest the hypothesis that NMDA hypofunction may precede the onset of frank psychosis and be present during the prodromal phase. Chronic treatment with NMDA antagonists in the monkey leads to gradual development of apparent hallucinatory behavior (Linn et al., 1999). Subchronic administration of an NMDA antagonist led to altered basal and evoked dopamine release that persisted after drug discontinuation (Jentsch et al., 1997b). Thus, hallucinations in chronic schizophrenia may reflect the result of persistent NMDA dysfunction leading to secondary dopaminergic disruption. To the extent that this formulation is correct, it is possible that reversal of or compensation for NMDA deficits in prodromal patients might lead to arrest in the process leading to psychosis development, even if the therapeutic value in chronic patients were incomplete.

For purposes of the present invention, prodromal schizophrenia is identified or determined by a psychiatrist or other physician from the patient's abnormal or unusual thought content, suspiciousness, grandiosity, perceptual abnormalities, and/or disorganization of communication, all below the threshold of frank psychosis because of subsyndromal intensity, duration, or frequency; which symptoms have begun or worsened in the past year and which symptoms currently have occurred at least once per week over the last month.

See, Thomas L E and Woods S W. The schizophrenia prodrome: "A developmentally informed review and update for psychopharmacological treatment." *Child and Adolescent Psychiatric Clinics of North America* 2006; 15:109-133.

The inventor has been instrumental in developing and validating a psychiatric structured diagnostic interview for the schizophrenia prodrome (the SIPS) and a rating scale to monitor its severity (the SOPS). Several scientific publications on these instruments are cited in the Thomas and Woods review article, cited above.

The prodromal diagnosis, above, excludes frank schizophrenia as defined hereinbelow.

In Frank schizophrenia,

A. Two or more of the following symptoms have occurred:
(1) Delusions
(2) Hallucinations
(3) Grossly disorganized speech
(4) Grossly disorganized behavior
(5) Negative symptoms; along with B. Social/occupational dysfunction; such that C. The symptoms currently have continuously persisted for at least 6 months; and D. The symptoms are not due to schizoaffective disorder, mood disorder, substance abuse, or developmental or medical illness.

See, *Diagnostic and Statistical Manual of Mental Disorders, Fourth Edition*. American Psychiatric Association, Washington D.C., 1994, pp 285-6.

The term "NMDA/glycine site agonists" refer to NMDA/glycine site agonists which target NMDA hypofunction and can be used to treat prodromal schizophrenia according to the present invention. These agonists include glycine, D-serine, D-alanine, D-cycloserine (4-aminoisoxazolidin-3-one), pharmaceutically acceptable salts thereof and mono or di-amide/ester prodrug forms of these amino acids (where the amino group of the amino acid forms an amide group with a $C_2$-$C_{21}$ acyl group, and/or the carboxylic acid function of the amino acid forms an ester group with a $C_1$-$C_{20}$ alkyl group and, in the case of serine, the OH of the $CH_2OH$ side chain of serine forms an ester with a $C_2$-$C_{21}$ acyl group).

NMDA glycine site agonists which are amino acids as described above or their pharmaceutically acceptable salts or prodrug forms are represented by the structure:

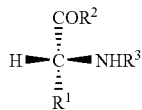

Where $R^1$ is H, $CH_3$ or $CH_2OR^4$;
$R^2$ is OH, a $C_1$-$C_{20}$ optionally substituted O-alkyl group, or is absent;
$R^3$ is H, or a $C_2$-$C_{21}$ optionally substituted acyl group; and
$R^4$ is H, a $C_2$-$C_{21}$ optionally substituted allyl group, or a —N— group which forms a five-membered heterocyclic group when bound to said CO group when $R^2$ is absent (forming D-cycloserine or a derivative);
or a pharmaceutically acceptable salt, solvate (including a hydrate) or polymorph thereof.

NMDA receptors are complex molecules that are composed of multiple subunits, termed NR1, NR2A-D, and NR3A-B, and that contain multiple binding sites including a site for the primary ligand (glutamate), as well as a modulatory site that is sensitive to the amino acids glycine and D-serine (Javitt, 2004b; Javitt and Zukin, 1991). Both glycine (Supplisson and Bergman, 1997) and D-serine (Hashimoto et al., 1992; Schell et al., 1995) are present in high concentration in mammalian brain and may represent endogenous ligands for the glycine binding site of the NMDA receptor complex.

At present, the site of the NMDA receptor that has proven most amenable to intervention has been the glycine-binding site, which serves as an allosteric site for regulation of glutamate binding. Glutamate, which serves as the primary neurotransmitter at NMDA receptors, is normally released in a phasic manner from presynaptic terminals and rapidly reabsorbed. Glycine and D-serine modulate glutamate binding in that the glycine site must be occupied for glutamate to have its effect. Glycine and D-serine bind to the NR1 NMDA receptor subunit (Foucaud et al., 2003; Miyazaki et al., 1999), whereas glutamate binding overlaps NR2 subunits. Administration of glutamate-site agonists leads to prolonged, non-physiological activation of glutamate receptors, including both NMDA and non-NMDA subtypes, and therefore leads to seizures and excitotoxicity. In contrast, the glycine site is occupied tonically by partially saturating concentrations of the endogenous brain amino acids glycine and D-serine. These amino acids are thought to be present at approximately half-saturating concentrations (Supplisson and Bergman, 1997), suggesting that exogenous stimulation of this site may lead to approximate doubling of the strength of NMDA activation in brain. Further, occupancy of the glycine site does not, by itself, lead to NMDA channel opening. Thus, glycine-site agonists potentiate NMDA neurotransmission only when glutamate is released, but do not maintain the channel in a prolonged, non-physiological open state.

Both glycine and D-serine appear to contribute to NMDA receptor function in most brain regions. Application of D-amino acid oxidase, which reduced brain D-serine concentrations by more than 90% without affecting glycine, reduced NMDA receptor responses by 50-70% (Mothet et al., 2000). Both glycine (Javitt et al., 1999) and D-serine (Contreras, 1990) reverse the effects of NMDA antagonists, and both glycine (Lu et al., 2001) and D-serine (Yang et al., 2003) support LTP. Further, although glycine and D-serine have similar effects on most NMDA receptors, receptors containing NR3A subunits may show differential sensitivity in that they are stimulated by glycine but inhibited by D-serine (Chatterton et al., 2002). Only a minority of NMDA receptors, however, contain NR3 subunits (Goebel and Poosch, 1999; Nishi et al., 2001), however, so the functional consequences of the differential glycine/D-serine effects are unclear. Glycine appears to enter the synapse primarily through diffusion, and its concentration is kept a receptor subsaturating levels by reuptake via the glycine T1 transporter; D-serine, on the other hand, is phasically released by astroglia (Wolosker et al., 2002). Taken together, this literature suggests that increasing glycine site activity at NMDA receptors could potentially relieve NMDA receptor hypofunction.

A class of compounds referred that could therapeutically relieve NMDA hypofunction in patients with prodromal schizophrenia can be referred to as NMDA/glycine-site agonists or glycine-site positive allosteric NMDA modulators. The amino acid glycine itself is one member of a class of compound. Other members of this category include D-alanine, D-serine and D-cycloserine (4-aminoisoxazolidin-3-one). Both glycine and D-serine are naturally-occurring compounds and full agonists at the glycine-binding site of the NMDA receptor. D-cycloserine is a synthetic compound that fortuitously cross-reacts with the NMDA-associated glycine-binding site. However, D-cycloserine is a mixed agonist/antagonist site, which shows agonist activity only in the presence of low brain glycine/D-serine concentrations. In clinical treatment, glycine and D-serine have shown moderate efficacy in established schizophrenia as adjunctive medications, primarily for residual negative symptoms, that appears to be more potent than similar effects of D-cycloserine. Glycine, D-alanine, D-serine, and D-cycloserine all act directly at the glycine site on the NMDA receptor and thus are termed direct agonists. Other members of the NMDA/glycine-site agonist class of compounds act indirectly by increasing the effects of direct agonists. These compounds can be termed NMDA/glycine-site indirect agonists. One such example is the amino acid sarcosine, which acts to increase synaptic glycine levels indirectly by blocking the reuptake of glycine at glial glycine transporter (glyT1) sites.

Clinical studies with NMDA/glycine site agonists in established schizophrenia. Although no previous studies have specifically treated the prodrome of schizophrenia with NMDA/glycine site agonists, several studies over the past decade have evaluated their potential role in chronic schizophrenia. The primary ligands available for clinical study to date include the endogenous brain compounds glycine and D-serine, as well as the synthetic compound D-cycloserine which fortuitously cross-reacts with the glycine binding site. As opposed to glycine, D-alanine and D-serine which are full NMDA agonists, however, D-cycloserine functions only as a partial agonist, leading to 40-60% of the activation seen with glycine, D-alanine or D-serine. Because of poor permeation into the brain and extensive peripheral metabolism, therapeutic doses of glycine are in the range of 30-60 g per day (D'Souza et al., 2000). D-Serine, which is less extensively metabolized peripherally, appears to be effective at doses as low as 2 g per day, although dose-response studies with this agent have not yet been conducted. D-cycloserine appears most effective when given at a dose of 50 mg/d. At higher doses, antagonist effects of D-cycloserine predominate, and clinical worsening of psychosis is typically observed (Goff et al., 1995).

When given at the above doses, results of placebo-controlled clinical trials conducted with NMDAR function enhancers have been generally consistent across studies. Studies with the full agonists D-serine (Javitt, 2004a; Tsai et al., 1998) and glycine (Heresco-Levy et al., 2004; Heresco-Levy et al., 1996; Heresco-Levy et al., 1999; Javitt et al., 2001) have demonstrated highly significant improvement in negative symptoms when these agents are added to typical antipsychotics, or newer atypicals, such as risperidone and olanzapine. The glycine T1 transporter inhibitor sarcosine, which would increase synaptic concentrations of the full agonist glycine, also has been shown to improve (Tsai et al., 2004b) negative symptoms. Although many investigators are most familiar with negative symptom benefits of these drugs, the level of positive symptom improvement has been significant in some studies although somewhat smaller (Heresco-Levy et al., 2004; Javitt, 2004a; Javitt et al., 2001; Tsai et al., 2004b). Studies with the partial agonist D-cycloserine have also demonstrated statistically significant results (Evins et al., 2002; Goff et al., 1999; Heresco-Levy et al., 2002), although the level of improvement has been more modest.

Interestingly, when the full agonists have been added to clozapine (Evins et al., 2000; Tsai et al., 1999), they do not separate from placebo, and when the partial agonist was added to clozapine (Goff et al., 1996), patients deteriorated, raising the possibility that the atypical effects of clozapine may already reflect significant glutamatergic potentiation (Javitt, 2004b).

At the recent American College of Neuropsychopharmacology meeting, there were two presentations of results that encourage circumspection about NMDA agonist approaches in chronic patients. First, the CONSIST study was presented, which randomized 157 chronic patients with persistent negative symptoms at four sites to adjunctive treatment with the full agonist glycine, the partial agonist D-cycloserine (4-aminoisoxazolidin-3-one), or placebo (Carpenter et al., 2004). There were no significant differences overall among groups. The second study presented at ACNP randomized 65 acutely exacerbated patients to D-serine vs sarcosine vs placebo in addition to antipsychotic (Tsai et al., 2004a). D-serine did not separate from placebo, while sarcosine did.

Although these results are cause for circumspection, they need not temper enthusiasm for investigating NMDA mechanisms in the treatment of the schizophrenia prodrome. Most importantly, it is certainly possible for NMDA agonists to have weaker or inconsistent effects in chronic patients and yet to be very beneficial in prodromal patients. NMDA receptor hypofunction over periods of chronic illness could lead to entrenched adaptations that persist even after the NMDA hypofunction is addressed. One possibility for such a mechanism would be the increased dopamine release that accompanies acute NMDA receptor blockade (Deutch et al., 1987; Jentsch et al., 1997a; Moghaddam et al., 1997). Subchronic administration of an NMDA antagonist lead to cognitive impairments and altered basal and evoked dopamine release that persisted after drug discontinuation (Jentsch et al., 1997b). Thus weak or inconsistent effects in chronic patients may not preclude substantial efficacy in prodromal patients.

In addition, these two studies are not necessarily the last word on the subject, even in chronic patients. The CONSIST study was the largest glycine trial in chronic patients so far, but results from the single largest trial do not always correspond with results from earlier smaller trials, for reasons that are not always clear (LeLorier et al., 1997). Four smaller previous studies with glycine had shown significant improvement relative to placebo. In the CONSIST study, treatment effects significantly differed across site, with one site showing active treatments better than placebo and another site that they were worse than placebo. Second, glycine levels in CONSIST were lower than expected, suggesting compliance problems. It is not clear yet why the new Tsai et al study of D-serine (Tsai et al., 2004a) found results conflicting with their previous trial (Tsai et al., 1998). One possibility is that the 2 gram per day dose, used in all the previous studies, is suboptimal and so leads to somewhat inconsistent effects.

Summary of Rationale for Treating Prodromal Schizophrenia with NMDA/Glycine Site Agonists.

The previous discussion may be summarized succinctly as follows:
1. The NMDA hypofunction model explains negative and cognitive dysfunction in chronic schizophrenia better than the dopamine model.
2. Negative symptoms and cognitive dysfunction appear to precede the emergence of positive symptoms in the schizophrenia prodrome.
3. Pre-existing NMDA hypofunction may contribute to emerging dopamine disruption.
4. Emerging dopamine disruption secondary to persistence of prodromal NMDA hypofunction may explain the later appearance of more severe positive symptoms such as hallucinations in chronic schizophrenia These considerations led me to inquire whether NMDA/glycine site agonist therapy might be more effective in the prodrome than in chronic patients and perhaps even more effective than dopamine D2 antagonists in the prodrome. I therefore treated 10 patients meeting criteria for the schizophrenia prodrome with the NMDA full agonist glycine, used alone without antipsychotic medication. The results have been very promising (see Reduction to Practice). To my knowledge, this represents the first attempt to use direct or indirect NMDA/glycine agonists for patients with the schizophrenia prodrome.

The term "glycine transporter inhibitor" or "glycine transporter-1 inhitor" is used throughout the specification to describe a compound which inhibits glycine transporter-1 receptors, and consequently increases concentrations of synaptic glycine, resulting in enhanced or potentiated NMDA receptor function. Glycine transporters belong to the Na+/Cl— dependent family of neurotransmitter transporters. Glycine transporter-1 (GlyT1) is found throughout the brain and is preferentially expressed by glial cells. This has led to the suggestion that GlyT1 is ideally distributed to modulate glycine concentrations of NMDA receptor expressing synapses. Compounds which inhibit or block glycine reuptake by inhibiting glycine transporter-1 may be used in the present invention to treat prodromal schizophrenia according to the present invention. Compounds which may be used in this manner include any compound which selectively inhibits GlyT1.

Preferred glycine transporter inhibitors for use in the present invention include sarcosine and derivative compounds according to the chemical structure:

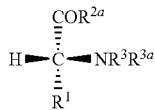

Where $R^1$ is H or $CH_3$;

$R^{2a}$ is OH, a $C_1$-$C_{20}$ optionally substituted alkoxy group (forming the ester), an optionally substituted $C_1$-$C_{20}$ hydrocarbyl group or an optionally substituted heterocyclic or heteroaromatic group;

$R^{3a}$ is $CH_3$ or together with $R^3$ or $R^1$ forms an optionally substituted heterocyclic or heteroaromatic group; and $R^3$ is H, a $C_2$-$C_{21}$ optionally substituted acyl group, or an optionally substituted $C_1$-$C_{20}$ (preferably an optionally substituted $C_5$-$C_{20}$) hydrocarbyl group, or an optionally substituted heterocyclic or heteroaromatic group, or a pharmaceutically acceptable salt, solvate (including a hydrate) or polymorph thereof is administered alone or preferably in combination with a pharmaceutically acceptable carrier, additive or excipient and optionally in combination with a NMDA glycine site agonist (as described above) to a patient or subject exhibiting symptoms of prodromal schizophrenia (initial or relapse) in order to treat said symptoms of prodromal schizophrenia and/or preferably to prevent or at least reduce the likelihood that the patient's prodromal schizophrenia will become frank psychosis.

Especially preferred compounds for use in the present invention include the compounds which are presented as compounds 2-43 in attached FIGS. 1A-E.

Preferred compounds according to the present invention which may be used as GlyT1 inhibitors to treat prodromal schizophrenia include compounds 243 of FIGS. 1A-E.

The present invention relates to the use of a NMDA/glycine site agonist and/or a glycine transporter inhibitor to treat prodromal schizophrenia in a patient. In this method of the present invention, a patient or subject exhibiting symptoms of prodromal schizophrenia (initial or relapse prodrome) is administered an effective amount of a compound selected from the group consisting of a NMDA/glycine site agonist, a glycine transporter-1 inhibitor or mixtures thereof, optionally in combination with a pharmaceutically acceptable carrier, additive or excipient, in order to treat the symptoms of prodromal schizophrenia (reduce the severity of and/or eliminate one or more, preferably a majority and more preferably virtually all symptoms of prodromal schizophrenia) or prevent or substantially reduce the likelihood that the patient's prodromal schizophrenia will become frank psychosis.

Compounds for use in the methods of the present invention have been described in detail hereinabove. Preferred compounds for use as NMDA glycine site agonists are amino acids or related derivatives according to the chemical structure:

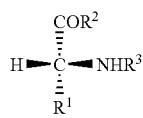

Where $R^1$ is H, $CH_3$ or $CH_2OR^4$;

$R^2$ is OH, a $C_1$-$C_{20}$ optionally substituted O-alkyl group, or is absent;

$R^3$ is H, or a $C_2$-$C_{21}$ optionally substituted acyl group; and $R^4$ is H, a $C_2$-$C_{21}$ optionally substituted alkyl group, or a —N— group which forms a five-membered heterocyclic group when bound to said CO group when $R^2$ is absent (forming D-cycloserine or a derivative); or a pharmaceutically acceptable salt, solvate (including a hydrate) or polymorph thereof which are administered alone or preferably in combination with a pharmaceutically acceptable carrier, additive or excipient and optionally in combination with a glycine transporter inhibitor to a patient or subject exhibiting symptoms of prodromal schizophrenia (initial or relapse) in order to treat said symptoms of prodromal schizophrenia and/or preferably to prevent or at least reduce the likelihood that the patient's prodromal schizophrenia will become frank psychosis. Preferred compounds useful as NMDA glycine site agonists include glycine, alanine or serine or any one or more of its prodrugs or pharmaceutically acceptable salts thereof.

In other aspects of the invention, alternative preferred compounds for use in the present method include a glycine transporter inhibitor (such as sarcosine or a derivative as presented below or any of the compounds 3-43 set forth in FIGS. 1A-E hereof) or a pharmaceutically acceptable salt, solvate (including a hydrate) or polymorph thereof to said patient exhibiting symptoms of prodromal (initial or relapse) schizophrenia (initial or relapse) in order to treat said symptoms of prodromal schizophrenia and/or preferably to prevent or at least reduce the likelihood that the patient's prodromal schizophrenia will become frank schiophrenia.

Additional preferred glycine transporter inhibitors include sarcosine and derivative compounds according to the chemical structure:

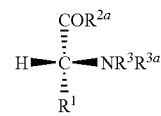

Where $R^1$ is H or $CH_3$;

$R^{2a}$ is OH, a $C_1$-$C_{20}$ optionally substituted alkoxy group (forming the ester), an optionally substituted $C_1$-$C_{20}$ hydrocarbyl group or an optionally substituted heterocyclic or heteroaromatic group;

$R^{3a}$ is $CH_3$ or together with $R^3$ or $R^1$ forms an optionally substituted heterocyclic or heteroaromatic group; and $R^3$ is H, a $C_2$-$C_{21}$ optionally substituted acyl group, or an optionally substituted $C_1$-$C_{20}$ (preferably an optionally substituted $C_5$-$C_{20}$) hydrocarbyl group, or an optionally substituted heterocyclic or heteroaromatic group, or a pharmaceutically acceptable salt, solvate (including a hydrate) or polymorph thereof is administered alone or preferably in combination with a pharmaceutically acceptable carrier, additive or excipient and optionally in combination with a NMDA glycine site agonist (as described above) to a patient or subject exhibiting symptoms of prodromal schizophrenia (initial or relapse) in order to treat said symptoms of prodromal schizophrenia and/or preferably to prevent or at least reduce the likelihood that the patient's prodromal schizophrenia will become frank psychosis.

Preferred glycine transporter-1 inhibitors for use in the present invention include, those which are described in the literature as being useful in the treatment of schizophrenia. Especially preferred compounds for use in the present invention include the compounds which are presented as compounds 2-43 in attached FIGS. 1A-E, as well as other compounds which may be gleaned from patents and patent applications/publications US2002426364; US2002169197; EP12842357; WO2003053942; WO2004096761; WO2003031435; DE10315570 (2004); WO2003055478; WO2004113280; WO2004112787; WO2004113301; WO2005049023; WO2003089411; WO2004013100; WO2004013101; WO2005037783; WO2005037792; WO2005037781; WO2005037782; WO205037785; WO2004072034; WO2005014563; WO2005023260; WO2005023261; WO2005040166; WO2005058882; WO2005058885; WO2005058317; WO2005046601; WO2003087086; WO2003076420; and WO2004022528, relevant portions of which references are incorporated herein. See also, Sur & Kinney, *Exper. Opin. Investig. Drugs*, 13(5), 515-521 (2004); Kenji Hashimoto, *Recent Patents on CNS Drug Discovery*, I, 43-53 (2006) and Harsing, et al., *Current Medicinal Chemistry*, Volume 13, Number 9, April 2006, pp. 1017-1044(28). ORG-24461, another glycine transporter-1 inhibitor, is also useful in the present invention.

Pharmaceutical compositions according to the present invention comprise an effective amount of one or more compounds according to the present invention optionally in combination with a pharmaceutically acceptable additive, carrier or excipient.

In another aspect, the present invention is directed to the use of one or more compounds according to the present invention in a pharmaceutically acceptable carrier, additive or excipient at a suitable dose ranging from about 0.05 to about 100 mg/kg of body weight per day, preferably within the range of about 0.1 to 50 mg/kg/day, most preferably in the range of 1 to 20 mg/kg/day. The desired dose may conveniently be presented in a single dose or as divided doses administered at appropriate intervals, for example as two, three, four or more sub-doses per day.

Ideally, the active ingredient should be administered to achieve effective peak plasma concentrations of the active compound within the range of from about 0.05 to about 5 uM. This may be achieved, for example, by the intravenous injection of about a 0.05 to 10% solution of the active ingredient, optionally in saline, or orally administered as a bolus containing about 1 mg to about 5 g, preferably about 5 mg to about 500 mg of the active ingredient, depending upon the active compound and its intended target. Desirable blood levels may be maintained by a continuous infusion to preferably provide about 0.01 to about 2.0 mg/kg/hour or by intermittent infusions containing about 0.05 to about 15 mg/kg of the active ingredient. Oral dosages, where applicable, will depend on the bioavailability of the compounds from the GI tract, as well as the pharmacokinetics of the compounds to be administered. While it is possible that, for use in therapy, a compound of the invention may be administered as the raw chemical, it is preferable to present the active ingredient as a pharmaceutical formulation, presented in combination with a pharmaceutically acceptable carrier, excipient or additive.

Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

Formulations containing the compounds of the invention may take the form of solid, semi-solid, lyophilized powder, or liquid dosage forms, such as, for example, tablets, capsules, powders, sustained-release formulations, solutions, suspensions, emulsions, sup-positories, creams, ointments, lotions, aerosols or the like, preferably in unit dosage forms suitable for simple administration of precise dosages.

The compositions typically include a conventional pharmaceutical carrier, additive or excipient and may additionally include other medicinal agents, carriers, and the like. Preferably, the composition will be about 0.05% to about 75-80% by weight of a compound or compounds of the invention, with the remainder consisting of suitable pharmaceutical additives, carriers and/or excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20%), and optional pharmaceutical additives, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion. The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Methods for preparing such dosage forms are known or will be apparent to those skilled in the art; for example, see "Remington's Pharmaceutical Sciences" (17th Ed., Mack Pub. Co, 1985). The person of ordinary skill will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients, preferably other NMDA glycine site agonists or glycine transporter-1 inhibitors in the treatment of prodromal schizophrenia Effective amounts or concentrations of each of the active compounds are to be included within the pharmaceutical compositions according to the present invention.

The individual components of such combinations may be administered either sequentially or simultaneously in separate or combined pharmaceutical formulations.

When one or more of the compounds according to the present invention is used in combination with a second therapeutic agent active the dose of each compound may be either the same as or differ from that when the compound is used alone. Appropriate doses will be readily appreciated by those skilled in the art.

In method aspects according to the present invention, one or more pharmaceutical compositions according to the present invention may be administered to a patient in the treatment or prevention of any disease state or condition previously mentioned. An effective amount of a NMDA glycine site agonist and/or a glycine transporter-1 inhibitor compound is administered to a patient exhibiting symptoms of prodromal Schizophrenia in order to treat said symptoms of Schizophrenia and reduce or eliminate the likelihood that said prodromal Schizophrenia will deteriorate to frank schizophrenia. Preferred compounds for use in the present invention include glycine, D-alanine, D-serine, D-cycloserine or a pharmaceutically acceptable salt thereof as NMDA glycine site agonists or any of the glycine transporter-1 inhibitor compounds (2-43) which are depicted in FIGS. 1A-E.

Pharmaceutical compositions according to the present invention comprise an effective amount of one or more compounds otherwise described herein optionally in combination with a pharmaceutically acceptable carrier, additive or excipient, and further optionally in combination with at least one additional NMDA glycine site agonist or glycine transporter-1 inhibitor or other active agent. In this aspect of the invention, multiple compounds may be advantageously formulated to be coadministered for the treatment of prodromal schizophrenia.

The individual components of such combinations as described above may be administered either sequentially or simultaneously in separate or combined pharmaceutical formulations. When one or more of the compounds according to the present invention is used in combination with a second therapeutic agent active the dose of each compound may be either the same as or differ from that when the compound is used alone. Appropriate doses will be readily appreciated by those skilled in the art.

EXAMPLES

The inventor of the present invention enrolled 10 prodromal patients in an eight-week open label trial of oral glycine. The patients were seven males and three females, whose mean±sd age was 17.3±3.3 years. All ten patients met schizophrenia prodrome diagnostic criteria, attenuated positive symptom subgroup, according to the Structured Interview for Prodromal Syndromes (Miller et al., 2002). The mean Scale of Prodromal Symptoms (SOPS) total score at baseline was 39.7, and the positive and negative subscale score means were respectively 11.3 and 12.4 (Table 1). These demographics and symptom scores are typical of prodromal samples recruited in previous work (Miller et al., 2003b).

TABLE 1

Glycine group SOPS scores at baseline, endpoint (LOCF), and endpoint change.

| SOPS | | POS | NEG | DIS | GEN | TOTAL |
| --- | --- | --- | --- | --- | --- | --- |
| BASE | mean | 11.3 | 12.4 | 6.5 | 9.5 | 39.7 |
| | sd | 3.3 | 5.5 | 2.5 | 4.1 | 11.8 |
| | n | 10 | 10 | 10 | 10 | 10 |
| END | mean | 5.6 | 9.4 | 3.4 | 6.0 | 24.4 |
| | sd | 4.3 | 6.5 | 1.9 | 3.9 | 12.8 |
| | n | 10 | 10 | 10 | 10 | 10 |
| CHANGE | mean | −5.7 | −3.0 | −3.1 | −3.5 | −15.3 |
| | sd | 5.2 | 4.1 | 3.0 | 3.1 | 11.0 |
| | n | 10 | 10 | 10 | 10 | 10 |
| | effect size | 1.10 | 0.74 | 1.05 | 1.12 | 1.39 |
| | exact p | 0.007 | 0.04 | 0.009 | 0.006 | 0.002 |

Glycine was administered orally as powder mixed with water at a dose titrated to 0.4 g/kg BID by week two. Concomitant medications were continued so long as there had been no dose adjustments in the eight weeks prior to enrollment and the patient continued to meet prodromal symptomatic criteria at baseline. Efficacy was assessed using the Scale of Prodromal Symptoms (SOPS). The SOPS consists of 19 items, each scored 0-6, and yields a total score and positive symptom (5 items), negative symptom (six items), disorganization (4 items), and general symptom (4 items) subscale scores. The content validity of the subscale scores has been demonstrated empirically through factor analysis (Hawkins et al., 2004b). High levels of inter-rater reliability have demonstrated when using the SOPS, with published intraclass correlations in the excellent range for 16/19 (Miller et al., 2003a).

Figure 2:
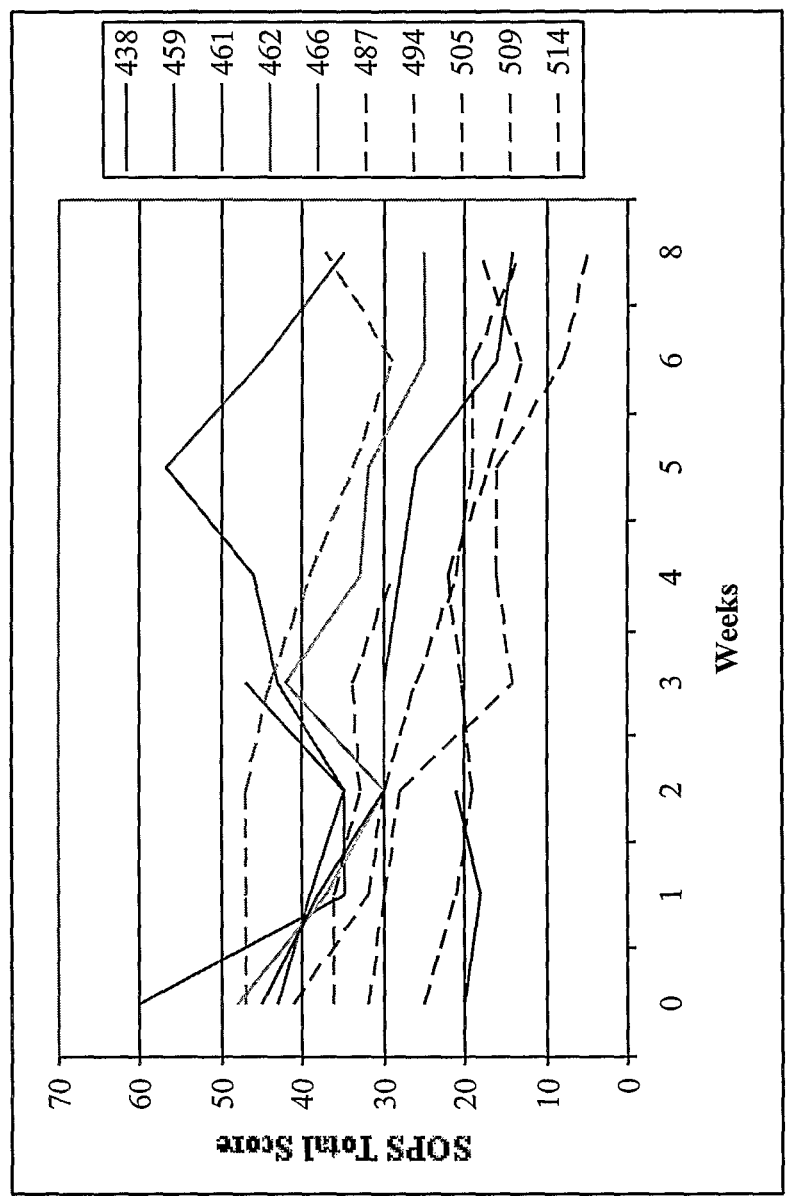
FIG. 2 shows SOPS total scores over time for each prodromal patient treated with glycine in the examples section of the present application
Figure 3:
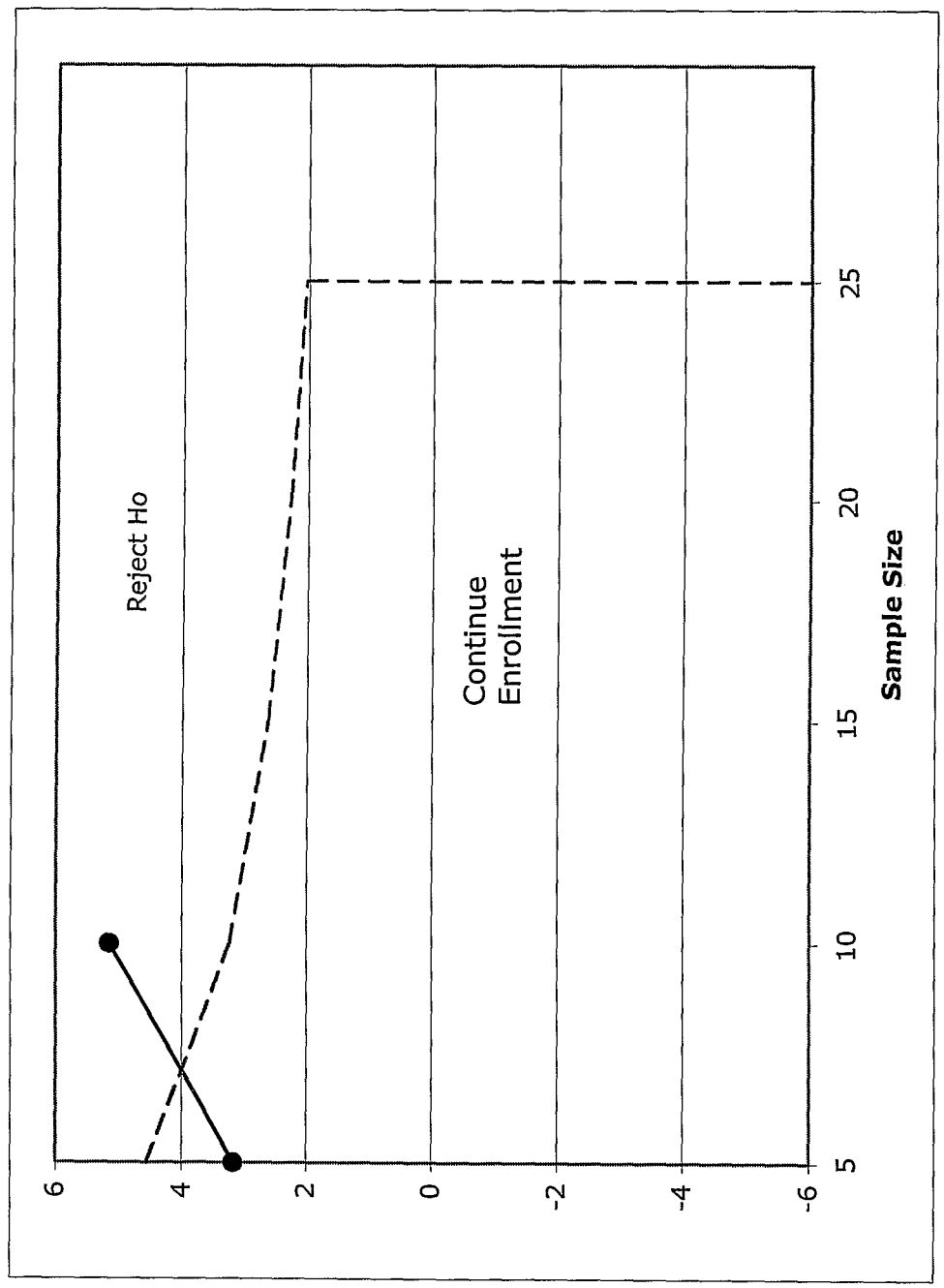
FIG. 3 shows the sequential monitoring vs historical placebo. The method evaluates sufficiency (sufficient evidence to suggest efficacy) which is depicted in FIG. 3. The y-axis shows the T score of the glycine-historical placebo difference. After 10 subjects the data crossed the boundary the rejection region for the null hypothesis, indicating evidence of superiority to historical placebo.
Figure 4:
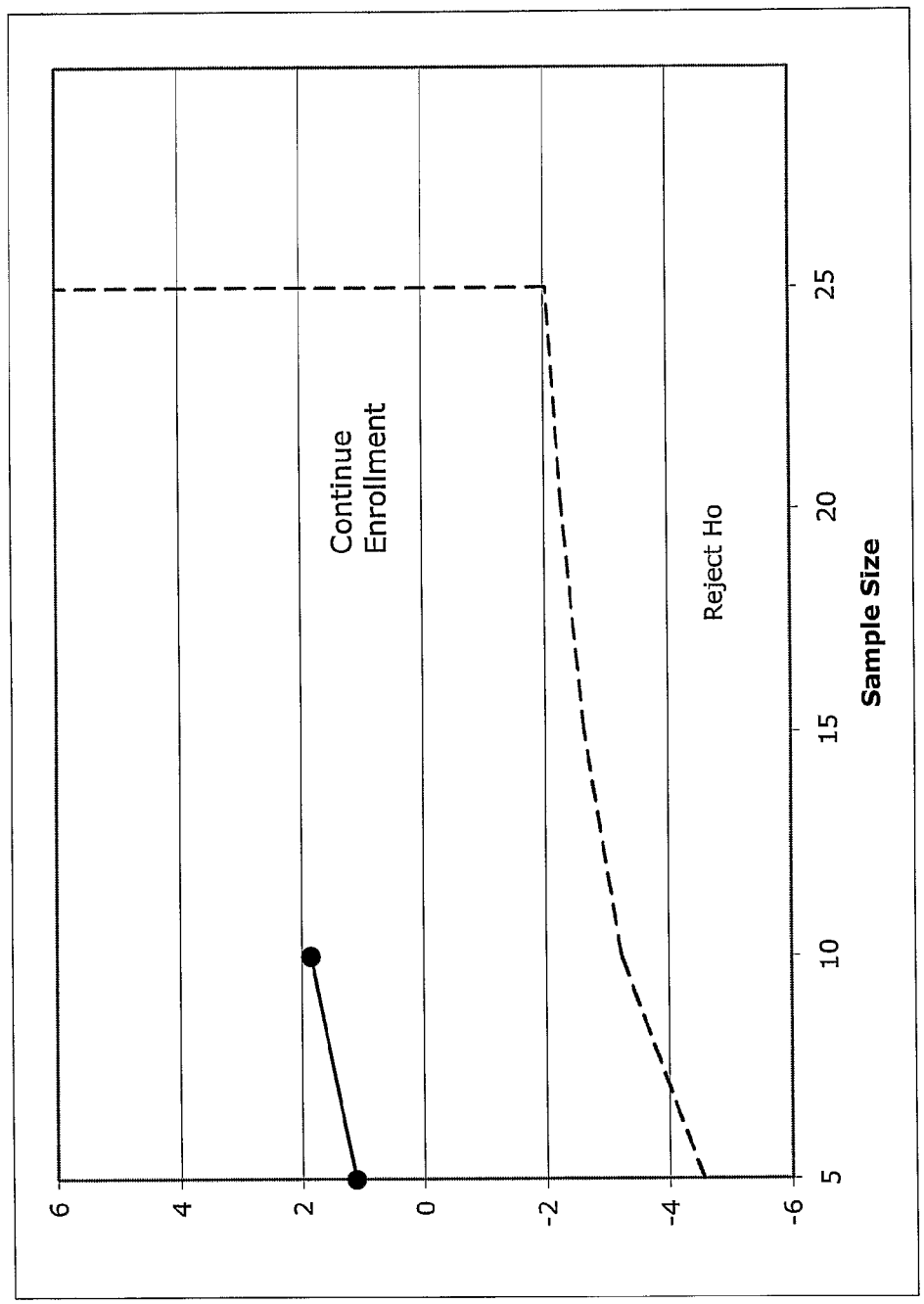
FIG. 4 shows method evaluating for inferiority to historical olanzapine to evaluate futility (sufficient evidence to suggest inferiority to an existing treatment).

Patient disposition. Seven of ten patients completed the planned eight weeks (FIG. 2). Of the remaining three, one dropped due to lack of efficacy after three weeks. The remaining two dropped after weeks 2 and 5 due to transportation or family difficulties.

Categorical outcomes. Of the seven completers, three met early remission criteria during the 8 weeks on glycine (#s 466, 505, and 514 in FIG. 2). These criteria required all five positive symptom ratings to be below the prodromal range (2 or below). Of the four completers who did not meet early remission criteria, three showed modest improvement, and one substantial improvement (#487). Of the three drop-outs, one et al., 2003). These provide the only placebo treatment data reported in prodromal patients to date.

TABLE 3

MMRM-based within group improvement at 8 weeks.

| SOPS Improvement | POS | NEG | DIS | GEN | TOTAL |
|---|---|---|---|---|---|
| Glycine (n = 10)[a] | 7.4 ± 3.2*** | 3.0 ± 5.2* | 3.9 ± 2.2** | 4.1 ± 3.5** | 18.2 ± 9.9*** |
| Olanzapine (n = 30)[b] | 2.9 ± 6.0** | 4.6 ± 7.3*** | 2.0 ± 3.8** | 3.3 ± 4.6*** | 12.4 ± 18.3*** |
| Placebo (n = 29)[b] | 0.8 ± 6.0 | 0.7 ± 7.4 | −0.1 ± 3.8 | 2.2 ± 4.6 | 2.1 ± 18.2 |

[a]data from current study.
*$p < .10$,
**$p < .01$,
***$p < .001$, within group, two-tailed.
[b]data from previous study.
*$p < .10$,
**$p < .01$,
***$p < .001$, within group, two-tailed.
[c]data from previous study. All n.s., within group, two-tailed.

showed no change and two modest improvement prior to dropping out. None of the glycine-treated patients converted to psychosis. In our untreated samples, typically 25% of patients convert to psychosis in 8 weeks.

Group SOPS change analysis. In the last-observation-carried-forward (LOCF) analysis (Table 1), patients improved significantly as a group on the total score and on all four subscales. The largest within group effect size was seen for the SOPS total score. The effect sizes observed with glycine are substantially larger than those observed in my parallel studies with other medications (Table 2). Data for the placebo and olanzapine samples shown are from the published double blind randomized comparison of olanzapine vs placebo (Woods et al., 2003). Data for ethyl-EPA (an omega-3 fatty acid) are from an ongoing unpublished open label trial that follows a design nearly identical to the current glycine pilot study. The very large differences between the glycine effect sizes and the placebo effect sizes provide strong support for efficacy. The large differences between the glycine effect sizes and the olanzapine effect sizes are also impressive. In addition, the large differences between the current open-label glycine and the open-label omega-3 fatty acid effect sizes suggest that a substantial degree of the improvement seen with glycine may be attributed to the drug and not to patient and rater expectations related to an open-label design.

TABLE 2

LOCF within group effect sizes at 8 weeks with four treatments.

| SOPS LOCF Effect Size | POS | NEG | DIS | GEN | TOTAL |
|---|---|---|---|---|---|
| Glycine (n = 10) | 1.10 | 0.74 | 1.05 | 1.12 | 1.39 |
| Placebo (n = 29) | 0.10 | 0.24 | 0.11 | 0.59 | 0.27 |
| Olanzapine (n = 30) | 0.55 | 0.34 | 0.33 | 0.49 | 0.51 |
| Ethyl-EPA (n = 7) | 0.47 | 0.24 | −0.05 | −0.17 | 0.18 |

MMRM analysis. In addition to the LOCF analyses, I also conducted mixed-model repeated-measures analysis (MMRM (Woods et al., 2003) with patient as a random effect and using baseline score as a covariate. In these analyses (Table 3), patients improved significantly as a group on the total score and on 3/4 subscales. The largest within group effect size was seen for the SOPS total score, with the least robust for the negative symptom subscale and intermediate effect sizes for the positive symptom, disorganization, and general symptom subscales. The placebo and olanzapine comparison samples are drawn from a separate study (Woods et al., 2003). These provide the only placebo treatment data reported in prodromal patients to date.

This trial was sequentially monitored so that it could be discontinued if interim results showed evidence of futility or sufficiency. To accomplish this we modified for the one sample case the sequential monitoring method of O'Brien and Fleming that protects the overall alpha from type two error due to multiple looks (Woods and McGlashan, 2002). This method evaluates the single sample for superiority to external placebo to evaluate sufficiency (sufficient evidence to suggest efficacy, FIG. 3) and for inferiority to olanzapine to evaluate futility (sufficient evidence to suggest inferiority to an existing treatment, FIG. 4). Analyses were planned every 5 patients. Improvement with glycine crossed the decision boundary for sufficiency after 10 patients (FIG. 3), providing evidence clearly suggestive of efficacy.

REFERENCES

Abi-Saab W M, D'Souza D C, Moghaddam B, Krystal J H (1998) The NMDA antagonist model for schizophrenia—promise and pitfalls. Pharmacopsychiatry 31:104-109.

Adler C M, Goldberg T E, Malhotra A K, Pickar D, Breier A (1998) Effects of ketamine on thought disorder, working memory, and semantic memory in healthy volunteers. Biological Psychiatry 43:811-816.

Barnes T R E, Hutton S B, Chapman M J, Mutsatsa S, Puri B K, Joyce E M (2000) West London first episode study of schizophrenia: Clinical correlates of duration of untreated psychosis. British Journal of Psychiatry 177:207-211.

Belger A, Krystal J H, et al (in preparation).

Bleuler E (1911) Dementia Praecox or the Group of the Schizophrenias. New York: International Universities Press.

Breier A, Adler C M, Weisenfeld N, Su T P, Elman L Picken L, Malhotra A K, Pickar D (1998) Effects of NMDA antagonism on striatal dopamine release in healthy subjects: application of a novel PET approach. Synapse 29:142-147.

Carpenter W T, Buchanan R W, Javitt D C, Marder S R, Schooler N R, Heresco-Levy U, Gold J M (2004) Is glutamatergic therapy really efficacious in schizophrenia? (abstract). Neuropsychopharmacology 29:S110.

Chatterton J E, Awobuluyi M, Premkumar L S, Takahashi H, Talantova M, Shin Y, Cui J, Tu S, Sevarino K A, Nakanishi N, Tong G, Lipton S A, Zhang D (2002) Excitatory glycine receptors containing the NR3 family of NMDA receptor subunits. Nature. 415:793-798.

Chen E Y H, Dunn E L W, Chen R L Y, Chung K F, Tang W N, Chan W F, Miao Y K, Yeung W S, Wong C K (1999) Duration of untreated psychosis and symptomatic outcome among first episode schizophrenic patients in Hong Kong. Schizphrenia Research 36:15.

Contreras P C (1990) D-serine antagonized phencyclidine- and MK-801-induced stereotyped behavior and ataxia. Neurophammacology 29:291-293.

Cornblatt B A, Lencz T, Smith C W, Correll C U, Auther A M, Nakayama E (2003) The schizophrenia prodrome revisited: A neurodevelopmental perspective. Schizophrenia Bulletin 29:633-651.

Coyle J T, Tsai G (2004) NMDA receptor function, neuroplasticity, and the pathophysiology of schizophrenia. International Review of Neurobiology 59:491-515.

Craig T J, Bromet E J, Fennig S, Tanenberg-Karant M, Lavelle J, Galambos N (2000) Is there an association between duration of untreated psychosis and 24-month clinical outcome in a first-admission series? American Journal of Psychiatry 157:60-66.

D'Souza D C, Gil R, Cassello K, Morrissey K, Abi-Saab D, White J, Sturwold R, Bennett A, Karper L P, Zuzarte E, Charney D S, Krystal J H (2000) IV glycine and oral D-cycloserine effects on plasma and CSF amino acids in healthy humans. Biological Psychiatry. 47:450-462.

Deutch A Y, Tam S Y, Freeman A S, Bowers M B, Jr., Roth R H (1987) Mesolimbic and mesocortical dopamine activation induced by phencyclidine: contrasting pattern to striatal response. European Journal of Pharmacology 134: 257-264.

Domino E F, Luby E D (1981) Abnormal mental states induced by phencyclidine as a model for schizophrenia. In Domino E F (ed), PCP (Phencyclidine): Historical and Current Perspectives. Ann Arbor, Mich.: NPP Books, pp 401-418.

Evins A E, Amico E, Posever T A, Toker R, Goff D C (2002) D-Cycloserine added to risperidone in patients with primary negative symptoms of schizophrenia. Schizophrenia Research. 56:19-23.

Evins A E, Fitzgerald S M, Wine L, Rosselli R, Goff D C (2000) Placebo-controlled trial of glycine added to clozapine in schizophrenia. American Journal of Psychiatry 157:826-828.

Foucaud B, Laube B, Schemm R, Kreimeyer A, Goeldner M, Betz H (2003) Structural model of the N-methyl-D-aspartate receptor glycine site probed by site-directed chemical coupling. Journal of Biological Chemistry 278:24011-24017.

Goebel D J, Poosch M S (1999) NMDA receptor subunit gene expression in the rat brain: a quantitative analysis of endogenous mRNA levels of NR1Com, NR2A, NR2B, NR2C, NR2D and NR3A. Brain Research. Molecular Brain Research 69:164-170.

Goff D C, Tsai G, Levitt J, Amico E, Manoach D, Schoenfeld D A, Hayden D L, McCarley R, Coyle J T (1999) A placebo-controlled trial of D-cycloserine added to conventional neuroleptics in patients with schizophrenia.[see comment]. Archives of General Psychiatry 56:21-27.

Goff D C, Tsai G, Manoach D S, Coyle J T (1995) Dose-finding trial of D-cycloserine added to neuroleptics for negative symptoms in schizophrenia. American Journal of Psychiatry 152:1213-1215.

Goff D C, Tsai G, Manoach D S, Flood J, Darby D G, Coyle J T (1996) D-cycloserine added to clozapine for patients with schizophrenia. American Journal of Psychiatry 153: 1628-1630.

Hafner H, Maurer K, Loffler W, Riecher-Rossler A (1993) The influence of age and sex on the onset and early course of schizophrenia. Br J Psychiatry 162:80-86.

Hashimoto A, Nishikawa T, Hayashi T, Fujii N, Harada K, Oka T, Takahashi K (1992) The presence of free D-serine in rat brain. FEBS Letters 296:33-36.

Hawkins K A, Addington J, Keefe R S E, Christensen B, Perkins D O, Zipurksy R, Woods S W, Miller T J, Marquez E, Breier A, McGlashan T H (2004a) Neuropsychological status of subjects at high risk for a first episode of psychosis. Schizophrenia Research 67:115-122.

Hawkins K A, Quinlan D, Miller T J, McGlashan T H, Zipursky R B, Perkins D O, Addington J, Woods S W (2004b) Factorial structure of the scale of prodromal symptoms. Schizophrenia Research 68:339-347.

Heresco-Levy U, Ermilov M, Lichtenberg P, Bar G, Javift D C (2004) High-dose glycine added to olanzapine and risperidone for the treatment of schizophrenia. Biological Psychiatry. 55:165-171.

Heresco-Levy U, Ennilov M, Shimoni J, Shapira B, Silipo G, Javitt D C (2002) Placebo-controlled trial of D-cycloserine added to conventional neuroleptics, olanzapine, or risperidone in schizophrenia. American Journal of Psychiatry 159:480-482.

Heresco-Levy U, Javitt D C, Ermilov M, Mordel C, Horowitz A, Kelly D (1996) Double-blind, placebo-controlled, crossover trial of glycine adjuvant therapy for treatment-resistant schizophrenia. British Journal of Psychiatry 169: 610-617.

Heresco-Levy U, Javitt D C, Ermilov M, Mordel C, Silipo G, Lichtenstein M (1999) Efficacy of high-dose glycine in the treatment of enduring negative symptoms of schizophrenia Archives of General Psychiatry 56:29-36.

Ho B C, Andreasen N C, Flaum M, Nopoulos P, Miller D (2000) Untreated initial psychosis: its relation to quality of life and symptom remission in first-episode schizophrenia. American Journal of Psychiatry 157:808-815.

Javitt D C (2004a) D-serine as add-on pharmacotherapy to risperidone and olanzapine for treatment refractory schizophrenia: personal communication.

Javitt D C (2004b) Glutamate as a therapeutic target in psychiatric disorders. 9:984-997.

Javitt D C, Balla A, Sershen H, Lajtha A (1999) A. E. Bennett Research Award. Reversal of phencyclidine-induced effects by glycine and glycine transport inhibitors. Biological Psychiatry 45:668-679.

Javitt D C, Silipo G, Cienfuiegos A, Shelley A M, Bark N, Park M, Lindenmayer J P, Suckow R, Zukin S R (2001) Adjunctive high-dose glycine in the treatment of schizophrenia. International Journal of Neuropsychopharmacology 4:385-391.

Javitt D C, Zukin S R (1991) Recent advances in the phencyclidine model of schizophrenia[see comment]. American Journal of Psychiatry 148:1301-1308.

Jentsch J D, Elsworth J D, Redmond D E, Jr., Roth R H (1997a) Phencyclidine increases forebrain monoamine metabolism in rats and monkeys: modulation by the isomers of HA966. Journal of Neuroscience 17:1769-1775.

Jentsch J D, Redmond D E, Jr., Elsworth J D, Taylor J R, Youngren K D, Roth R H (1997b) Enduring cognitive deficits and cortical dopamine dysfunction in monkeys after long-term administration of phencyclidine. Science 277:953-955.

Kapur S, Remington G (2001) Dopamine D(2) receptors and their role in atypical antipsychotic action: still necessary and may even be sufficient. Biological Psychiatry 50:873-883.

Kegeles L S, Abi-Dargham A, Zea-Ponce Y, Rodenhiser-Hill J, Mann J J, Van Heertum R L, Cooper T B, Carlsson A, Laruelle M (2000) Modulation of amphetamine-induced striatal dopamine release by ketamine in humans: implications for schizophrenia Biological Psychiatry 48:627-640.

Krystal J H, Karper L P, Seibyl J P, Freeman G K, Delaney R, Bremner J D, Heninger G R, Bowers M B, Jr., Charney D S (1994) Subanesthetic effects of the noncompetitive NMDA antagonist, ketamine, in humans. Psychotomimetic, perceptual, cognitive, and neuroendocrine responses. Archives of General Psychiatry 51:199-214.

Lahti A C, Holcomb H H, Medoff D R, Tamminga C A (1995a) Ketamine activates psychosis and alters limbic blood flow in schizophrenia. Neuroreport 6:869-872.

Lahti A C, Koffel B, LaPorte D, Tamminga C A (1995b) Subanesthetic doses of ketamine stimulate psychosis in schizophrenia. Neuropsychopharmacology 13:9-19.

Lahti A C, Weiler M A, Tamara Michaelidis B A, Parwani A, Tamminga C A (2001) Effects of ketamine in normal and schizophrenic volunteers. Neuropsychopharmacology 25:455-467.

LeLorier J, Gregoire G, Benhaddad A, Lapierre J, Derderian F (1997) Discrepancies between meta-analyses and subsequent large randomized, controlled trials. New England Journal of Medicine 337:536-542.

Lencz T, Smith C W, Auther A, Correll C U, Comblatt B (2004) Nonspecific and attenuated negative symptoms in patients at clinical high-risk for schizophrenia. Schizophrenia Research 68:37-48.

Lieberman J A, Perkins D, Belger A, Chakos M, Jarskog F, Boteva K, Gilmore J (2001) The early stages of schizophrenia: speculations on pathogenesis, pathophysiology, and therapeutic approaches. Biological Psychiatry 50:884-897.

Linn G S, O'Keeffe R T, Schroeder C E, Lifshitz K, Javitt D C (1999) Behavioral effects of chronic phencyclidine in monkeys.[erratum appears in Neuroreport 2000 Mar. 20; 11(4):inside back cover, 901]. Neuroreport 10:2789-2793.

Lu W Y, Man H Y, Ju W, Trimble W S, MacDonald J F, Wang Y T (2001) Activation of synaptic NMDA receptors induces membrane insertion of new AMPA receptors and LTP in cultured hippocampal neurons. Neuron 29:243-254.

Luby E D (1981) Phencyclidine revisited. In Domino E F (ed), PCP (Phencyclidine): Historical and Current Perspectives. Ann Arbor, Mich.: NPP Books, pp 25-30.

Malhotra A K, Pinals D A, Adler C M, Elman I, Clifton A, Pickar D, Breier A (1997) Ketamine-induced exacerbation of psychotic symptoms and cognitive impairment in neuroleptic-free schizophrenics. Neuropsychopharmacology 17:141-150.

Malhotra A K, Pinals D A, Weingartner H, Sirocco K, Missar C D, Pickar D, Breier A (1996) NMDA receptor function and human cognition: the effects of ketamine in healthy volunteers. Neuropsychopharmacology 14:301-307.

Marshall M, Lewis S, Lockwood A, Drake R, Croudace T, Jones P (2003) Systematic review of the association between duration of untreated psychosis and outcome in cohorts of first episode patients (abstract). Schizophrenia Research 70:27.

McGlashan T H (1998) Early detection and intervention of schizophrenia: rationale and research. Br J Psychiatry Suppl 172:3-6.

McGlashan T H, Johannessen J O (1996) Early detection and intervention with schizophrenia: rationale. Schizophrenia Bulletin 22:201-222.

McGlashan T H, Miller T J, Woods S W (2001) Pre-onset detection and intervention research in schizophrenic psychoses; Current estimates of benefits and risks. Schizophrenia Bulletin 27:563-570.

McGlashan T H, Zipursky R B, Perkins D O, Addington J, Woods S W, Miller T J, Lindborg S (2004) Olanzapine vs placebo for prodromal schizophrenia. Schizophrenia Research 67:6.

McGorry P (1998) Verging on reality. Br J Psychiatry Suppl 172:1-136.

McGorry P D, Yung A R, Phillips L J, Yuen H P, Francey S, Cosgrave E M, Germano D, Bravin J, McDonald T, Blair A, Adlard S, Jackson H (2002) Randomized controlled trial of interventions designed to reduce the risk of progression to first-episode psychosis in a clinical sample with subthreshold symptoms. Archives of General Psychiatry. 59:921-928.

Miller T J, McGlashan T H, Rosen J L, Somjee L, Markovitch P, Stein K, Woods S W (2002) Prospective diagnosis of the prodrome for schizophrenia: Preliminary evidence of interrater reliability and predictive validity using operational criteria and a structured interview. American Journal of Psychiatry 159:863-865.

Miller T J, McGlashan T H, Woods S W, Stein K, Driesen N, Corcoran C M, Hoffman R, Davidson L (1999) Symptom assessment in schizophrenic prodromal states. Psychiatric Quarterly 70:273-287.

Miller T J, McGlashan T M, Rosen J L, Cadenhead K, Cannon T, Ventura J, McFarlane W, Perkins D O, Pearlson G D, Woods S W (2003a) Prodromal assessment with the Structured Interview for Prodromal Syndromes and the Scale of Prodromal Symptoms: Predictive validity, inter-rater reliability, and training to reliability. Schizophrenia Bulletin 29:703-715.

Miller T J, Rosen J L, D'Andrea J, Woods S W, McGlashan T H (2004) Outcome of prodromal syndromes: SIPS predictive validity (abstract). Schizophrenia Research 67:44.

Miller T J, Zipursky R B, Perkins D O, Addington J, Woods S W, Hawkins K A, Hoffman R, Preda A, Epstein I, Addington D, Lindborg S, Tohen M, Breier A, McGlashan T H (2003b) A randomized double blind clinical trial of olanzapine vs placebo in patients at risk for being prodromally symptomatic for psychosis: II. Baseline characteristics of the "prodromal" sample. Schizophrenia Research 61:19-30.

Miyazaki J, Nakanishi S, Jingami H (1999) Expression and characterization of a glycine-binding fragment of the N-methyl-D-aspartate receptor subunit NR1. Biochemical Journal 340:687-692.

Moghaddam B, Adams B, Verma A, Daly D (1997) Activation of glutamatergic neurotransmission by ketamine: a novel step in the pathway from NMDA receptor blockade to dopaminergic and cognitive disruptions associated with the prefrontal cortex. Journal of Neuroscience 17:2921-2927.

Morrison A P, French P, Walford L, Lewis S W, Kilcommons A, Green J, Parker S, Bentall R P (2004) Cognitive therapy for the prevention of psychosis in people at ultra-high risk. Randomized controlled trial. British Journal of Psychiatry 184:291-297.

Mothet J P, Parent A T, Wolosker H, Brady R O, Jr., Linden D J, Fernis C D, Rogawski M A, Snyder S H (2000) D-serine is an endogenous ligand for the glycine site of the N-methyl-D-aspartate receptor. Proceedings of the National Academy of Sciences of the United States of America 97:4926-4931.

Murray C J L, Lopez A D (1996) The Global Burden of Disease: World Health Organization, Harvard University Press.

Nishi M, Hinds H, Lu H P, Kawata M, Hayashi Y (2001) Motoneuron-specific expression of NR3B, a novel NMDA-type glutamate receptor subunit that works in a dominant-negative manner. Journal of Neuroscience 21:1.

Norman R M, Malla A K (2001) Duration of untreated psychosis: a critical examination of the concept and its importance. Psychological Medicine. 31:381-400.

Preda A, Miller T J, Rosen J L, Somjee L, McGlashan T H, Woods S W (2002) Treatment histories of patients with a syndrome putatively prodromal for schizophrenia. Psychiatric Services 53:342-344.

Robinson D G, Woemer M G, Alvir A M J, Geisler S, Koreen A, Sheitman B, Chakos M, Mayerhoff D, Bilder R, Goldman R, Lieberman J A (1999) Predictors of treatment response from a first episode of schizophrenia or schizoaffective disorder. American Journal of Psychiatry 156:544-549.

Rosen J L, Woods S W, Miller T J, McGlashan T H (2002) Prospective observations of emerging psychosis. Journal of Nervous & Mental Disease 190:133-141.

Schell M J, Molliver M E, Snyder S H (1995) D-serine, an endogenous synaptic modulator: localization to astrocytes and glutamate-stimulated release. Proceedings of the National Academy of Sciences of the United States of America 92:3948-3952.

Stephenson J (1999) Schizophrenia researchers striving for early detection and intervention. JAMA 281:1877-1888.

Sullivan H S (1927) The onset of schizophrenia. American Journal of Psychiatry 7:105-134.

Supplisson S, Bergman C (1997) Control of NMDS Receptor Activation By a Glycine Transporter Co-Expressed in Xenopus Oocytes. Journal of Neuroscience 17:4580-4590.

Tsai G, Yang P, Chung L C, Lange N, Coyle J T (1998) D-serine added to antipsychotics for the treatment of schizophrenia.[see comment]. Biological Psychiatry 44:1081-1089.

Tsai G C, Lane H Y, Chang Y-C, Liu Y-C, Chiu C-C (2004a) Sarcosine (N-methylglycine) or D-serine add-on treatment for acute exacerbation of schizophrenia: a randomized, double-blind, placebo-controlled study (abstract). Neuropsychopharmacology 29:S229-230.

Tsai G C, Lane H Y, Yang P C, Chong M Y, Lange N (2004b) Glycine transporter I inhibitor, N-methylglycine (Sarcosine), added to antipsychotics for the treatment of schizophrenia. Biological Psychiatry 55:452-456.

Tsai G E, Yang P, Chung L C, Tsai I C, Tsai C W, Coyle J T (1999) D-serine added to clozapine for the treatment of schizophrenia. American Journal of Psychiatry 156:1822-1825.

Umbricht D, Schmid L, Koller R, Vollenweider F X Hell D, Javitt D C (2000) Ketamine-induced deficits in auditory and visual context-dependent processing in healthy volunteers: implications for models of cognitive deficits in schizophrenia. Archives of General Psychiatry 57:1139-1147.

Wolosker H, Panizzutti R, De Miranda J (2002) Neurobiology through the looking-glass: D-serine as a new glial-derived transmitter. Neurochemistry International. 41:327-332.

Woods S W, Breier A, Zipursky R B, Perkins D O, Addington J, Miller T J, Hawkins K A, Marquez E, David S R, Tohen M, McGlashan T H (2003) Randomized trial of olanzapine vs placebo in the symptomatic acute treatment of patients meeting criteria for the schizophrenic prodrome. Biological Psychiatry 54:453-464.

Woods S W, Martin A, Spector S G, McGlashan T H (2002) Effects of development on olanzapine-associated adverse events. Journal of the American Academy of Child and Adolescent Psychiatry 41:1439-1446.

Woods S W, McGlashan T H (2002) Sample size planning for prodromal intervention trials (abstract). Schizophrenia Research 53:40.

Woods S W, McGlashan T H (2005) Special issues in intervention: The early phases of schizophrenia. In Sadock B J, Sadock V A (eds), Comprehensive Textbook of Psychiatry. Baltimore, Md.: Lippincott Williams & Wilkins, pp 1550-1558.

Woods S W, Miller T J, McGlashan T H (2001) The prodromal patient: Both symptomatic and at risk. CNS Spectrums 6:223-232.

Yang Y, Ge W, Chen Y, Zhang Z, Shen W, Wu C, Poo M, Duan S (2003) Contribution of astrocytes to hippocampal long-term potentiation through release of D-serine. Proceedings of the National Academy of Sciences of the United States of America. 100:15194-15199.

Yung A R, Phillips U J, Yuen H P, Francey S M, McFarlane C A, Haflgren M, McGorry P D (2003) Psychosis prediction: 12-month follow up of a high-risk ("prodromal") group. Schizophrenia Research 60:21-32.

The invention claimed is:

1. A method of treating prodromal schizophrenia in a patient in need comprising administering to said patient an effective amount of a composition consisting essentially of a compound selected from the group consisting of glycine, D-alanine, D-serine, sarcosine, D-cycloserine, a pharmaceutically acceptable salt thereof or a mixture thereof in the absence of antipsychotic medication.

2. The method according to claim 1 wherein said compound is glycine or a pharmaceutically acceptable salt thereof.

3. The method according to claim 1 wherein said compound is a mixture of glycine or a pharmaceutically acceptable salt thereof and at least one additional compound selected from the group consisting of: D-alanine, D-serine, sarcosine and D-cycloserine or a pharmaceutically acceptable salt thereof.

4. A method of treating prodromal schizophrenia in a patient in need comprising administering to said patient an effective amount of a composition consisting essentially of glycine or a pharmaceutically acceptable salt thereof in the absence of antipsychotic medication.

* * * * *